US006855545B1

(12) United States Patent
Sands et al.

(10) Patent No.: US 6,855,545 B1
(45) Date of Patent: *Feb. 15, 2005

(54) INDEXED LIBRARY OF CELLS CONTAINING GENOMIC MODIFICATIONS AND METHODS OF MAKING AND UTILIZING THE SAME

(75) Inventors: Arthur T. Sands, The Woodlands, TX (US); Glenn A. Friedrich, The Woodlands, TX (US); Brian Zambrowicz, The Woodlands, TX (US); Allan Bradley, Houston, TX (US)

(73) Assignee: Lexicon Genetics Inc., The Woodlands, TX (US)

(*) Notice: Subject to any disclaimer, the term of this patent is extended or adjusted under 35 U.S.C. 154(b) by 146 days.

This patent is subject to a terminal disclaimer.

(21) Appl. No.: 09/639,453

(22) Filed: Aug. 15, 2000

Related U.S. Application Data

(60) Division of application No. 08/942,806, filed on Oct. 2, 1997, now Pat. No. 6,207,371, and a continuation of application No. 08/907,598, filed on Aug. 8, 1997, now Pat. No. 6,139,833, and a continuation-in-part of application No. 08/728,963, filed on Oct. 11, 1996, now abandoned, which is a continuation-in-part of application No. 08/728,867, filed on Oct. 4, 1996, now Pat. No. 6,136,566.

(51) Int. Cl.[7] .................. C12N 15/86; C12N 15/00; C12N 15/82; C12N 15/09; C12Q 1/68
(52) U.S. Cl. .................. 435/325; 435/7.1; 435/7.2; 435/6; 435/69.1; 435/254.2; 435/354; 435/455; 800/18; 800/21; 800/278; 536/23.1; 536/23.4; 536/23.5; 536/24.1
(58) Field of Search .................. 435/325, 5, 6, 435/7.1, 7.2, 455, 440, 69.1, 471, 320.1, 366; 800/18, 21, 278; 536/23.1, 23.4, 24.1, 24.2, 24.5

(56) References Cited

U.S. PATENT DOCUMENTS

| | | | |
|---|---|---|---|
| 4,109,496 A | 8/1978 | Allemann et al. | |
| 4,683,195 A | 7/1987 | Mullis et al. | |
| 4,683,202 A | 7/1987 | Mullis | |
| 4,800,159 A | 1/1989 | Mullis et al. | |
| 4,889,818 A | 12/1989 | Gelfand et al. | |
| 4,965,188 A | 10/1990 | Mullis et al. | |
| 5,023,171 A | 6/1991 | Ho et al. | |
| 5,066,584 A | 11/1991 | Gyllensten et al. | |
| 5,075,216 A | 12/1991 | Innis et al. | |
| 5,079,352 A | 1/1992 | Gelfand et al. | |
| 5,091,310 A | 2/1992 | Innis | |
| 5,104,792 A | 4/1992 | Silver et al. | |
| 5,364,783 A | 11/1994 | Ruley et al. | |
| 5,449,614 A | 9/1995 | Danos et al. | |
| 5,464,764 A | 11/1995 | Capecchi et al. | |
| 5,641,670 A | 6/1997 | Treco et al. | |
| 5,679,523 A | * 10/1997 | Li et al. .................. 435/6 |
| 5,830,707 A | 11/1998 | Bushman | |
| 6,136,566 A | * 10/2000 | Sands et al. .................. 435/69.7 |
| 6,139,833 A | 10/2000 | Burgess et al. | |
| 6,207,371 B1 | * 3/2001 | Zambrowicz et al. .................. 435/6 |

FOREIGN PATENT DOCUMENTS

| | | |
|---|---|---|
| GB | WO 88/01646 | 3/1988 |
| WO | WO 96/29411 | 9/1996 |
| WO | WO 96/37626 | 11/1996 |
| WO | WO 97/20038 | 6/1997 |
| WO | WO 98/07858 | 2/1998 |
| WO | WO 98/14614 | 4/1998 |
| WO | WO 98/20031 | 5/1998 |
| WO | WO 98/24918 | 6/1998 |

OTHER PUBLICATIONS

Yoshida et al. (Transgenic Research, Jul. 1995; 4:277–87.*
Nussaume et al. (Mol. Gen. Genet., Nov. 1995; 249:91–101.*
Gruber, et al. Expression of the Volvox gene encoding nitrate reductase: Mutation–dependent activation of cryptic splice sites and intron–enhanced gene expression from a cDNA. Plant Molecular Biology vol. 31:1–12, Aug. 21, 1996.*
U.S. Appl. No. 08/728,963, filed Oct. 11, 1996, Sands et al.
U.S. Appl. No. 08/942,806, filed Oct. 2, 1997, Sands et al.
U.S. Appl. No. 09/570,923, filed May 15, 2000, Sands et al.
Akam, 1987, *Development*, 101:1–22.
Akagi et al., 1997, *Nucleic Acids Res.*, 25:1766–1773.
Allen et al., 1988, *Nature*, 333:852–855.
Altschul et al., 1990, *J. Mol. Biol.*, 215:403–410.
Auch et al., 1990, *Nucleic Acids Res.*, 18(22):6743–6744.
Bandyopadhyay et al., 1984, *Mol Cell. Ciol.*, 4:749–754.
Barinaga, 1994, *Science*, 265:26–28.
Barnes et al., 1993, *TiPS*, 14:436–441.
Bellen et al., 1989, *Genes and Development*, 3:1288–1300.
Bier et al., 1989, *Genes and Development*, 3:1273–1287.
Bonadio, 1990, *Proc. Natl. Acad. Sci. USA*, 87:7145–7149.
Bonnerot et al., 1992, *J. Virol.*, 66:4982–4991.

(List continued on next page.)

*Primary Examiner*—Gerry Leffers
*Assistant Examiner*—Ramin Akhavan
(74) *Attorney, Agent, or Firm*—Finnegan, Henderson, Farabow, Garrett & Dunner, L.L.P.

(57) ABSTRACT

Methods and vectors (both DNA and retroviral) are provided for the construction of a Library of mutated cells. The Library will preferably contain mutations in essentially all genes present in the gene of the cells. The nature of the Library and the vectors allow for methods of screening for mutations in specific genes, and for gathering nucleotide sequence data from each mutated gene to provide a database of tagged gene sequences. Such a database provides a means to access the individual mutant cell clones contained in the Library. The invention includes the described Library, methods of making the same, and vectors used to construct the Library. Methods are also provided for accessing individual parts of the Library either by sequence or by pooling and screening. The invention also provides for the generation of non-human transgenic animals which are mutant for specific genes as isolated and generated from the cells of the Library.

6 Claims, 22 Drawing Sheets

OTHER PUBLICATIONS

Figure 1:
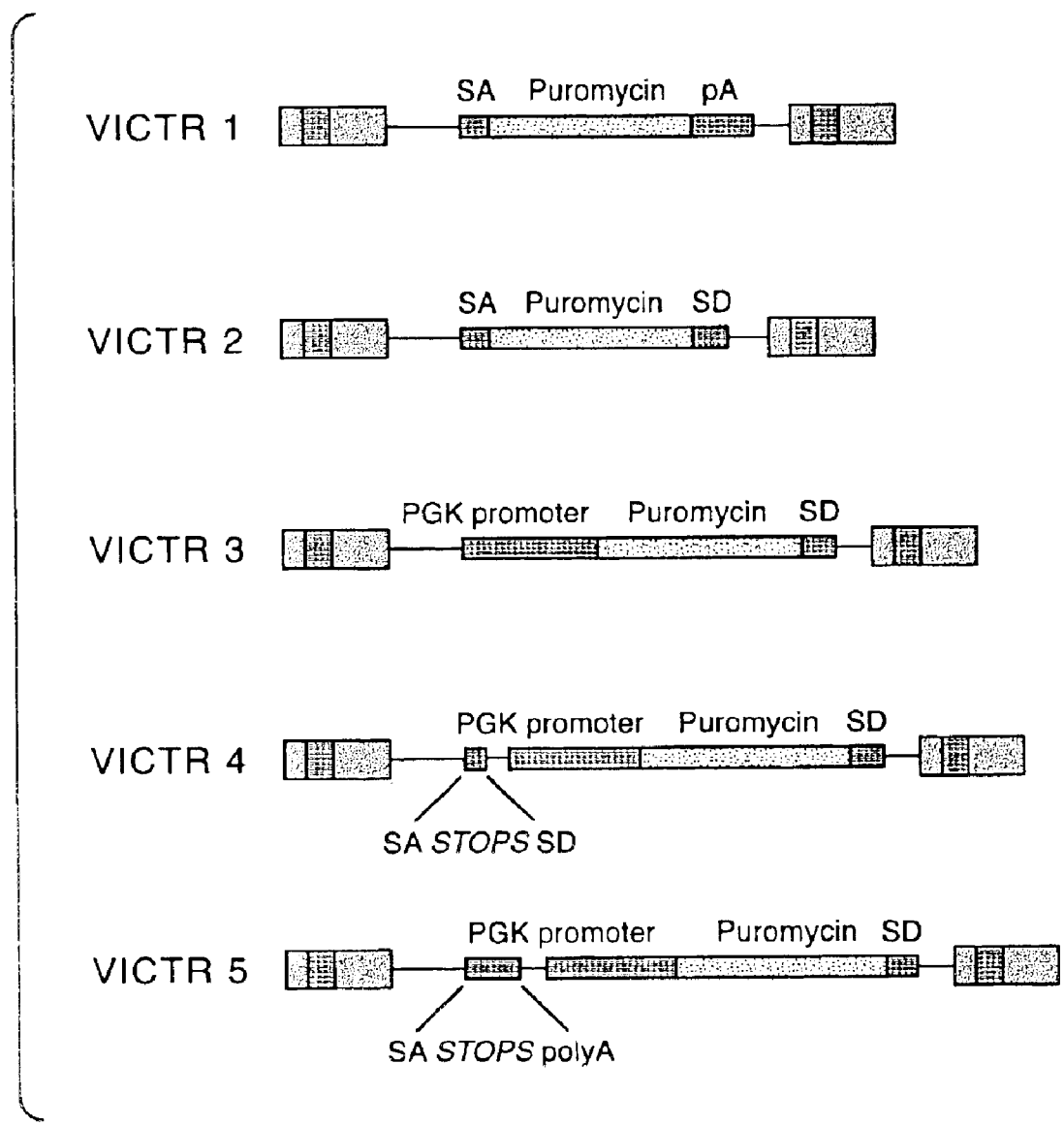

Bosselman et al., 1987, *Molec. Cell. Biol.*, 7:1797–1806.
Botsford et al., 1992, *Microbiol Rev.*, 56:100–122.
Bradley, 1991, *Cur. Opin. Biotech.*, 2:823–829.
Brenner et al., 1989, *Proc. Natl. Acad. Sci. USA*, 86:5517–5521.
Burke et al., 1995, *Development*, 121:333–346.
Bushman, 1994, *Proc. Natl. Acad. Sci. USA*, 91:9233–9237.
Bushman et al., 1997, *J. Virol.*, 458–464.
Campbell et al., 1997, *Theriogenology*, 47:63–72.
Chang et al., 1993, *Virology*, 193:737–747.
Chakraborty et al., 1993, *FASEB Journal*, 7:971–977.
Chen et al., 1994, *Genes and Development*, 8:2293–2301.
Chen et al., 1994, *Molec. Cell. Biol.*, 14:2140–2146.
Coulondre et al., 1977, *J. Mol. Biol.*, 117:577–606.
Dadoune, 1994, *Bull. Assoc. Anat.*, 78:33–40.
Danos et al., 1988, *Proc. Natl. Acad. Sci. USA*, 85:6460–6464.
Duyk et al., 1990, *Proc. Natl. Acad. Sci. USA*, 87:8995–8999.
Dymecki, 1996, *Gene*, 171:197–201.
Erlich, 1989, *PCR Technology: Principals and Applications of DNA Amplication*, Stockton Press.
Evans et al., 1997, *TIG*, 13(9):370–374.
Friedrich et al., 1991, *Genes and Development*, 5:1513–1523.
Friedrich et al., 1993, *Methods in Enzymology*, 225:681–701.
Frohman et al., 1988, *Proc. Natl. Acad. Sci. USA*, 85:8998–9000.
Frohman et al., 1994, *PCR Methods and Applications*, Cold Springs Harbor Press, 540–558.
Furth et al., 1994, *Proc. Natl. Acad. Sci. USA*, 91:9302–9306.
Gasca et al., 1995, *Developmental Genetics*, 17:141–154.
Goff, 1987, *Methods in Enzymology*, 151:489–502.
Goff, 1987, *Methods in Enzymology*, 152:469–481.
Gogos et al., 1996, *J. Cell Biol.*, 134(4):837–847.
Gogos et al., 1997, *J. Virol.*, 71(2):1644–1650.
Gossler et al., 1989, *Science*, 244:463–465.
Goulaouic et al., 1996, *J. Virol.*, 70:37–46.
Graham et al., 1991, *Methods Mol. Biol.*, 7:109–128.
Haas et al., 1993, *Gene*, 130:23–31.
Han et al., 1997, *Nature*, 386:296–299.
Helene, 1991, *Anticancer Drug Des.*, 6:569–584.
Helene et al., 1992, *Annals N.Y. Acad. Sci.*, 660:27–36.
Hicks et al., 1997, *Nature Genetics*, 16:338–344.
Hope, 1991, *Development*, 113:399–408.
Houghten et al., 1991, *Nature*, 354:84–86.
Ingraham et al., 1990, *Annu. Rev. Physiol.*, 52:773–791.
Innis et al., 1990, *PCR Protocols: A Guide to Methods and Applications*, Academic Press.
Jönsson et al., 1996, *Blood*, 87(5):1771–1779.
Katz et al., 1996, *Virology*, 217:178–190.
Kerr et al., 1989, *Cold Springs Harbor Symposia on Quantitative Biology*, LIV:767–776.
Khan et al., 1990, *Nucl. Acids Res.*, 19:851–860.
Kirchner et al., 1995, *Science*, 267:1488–1491.
Kozak, 1989, *J. Cell. Biol.*, 108:229–241.
Kulkosky et al., 1995, *Virology*, 206:448–456.
Lam et al., 1991, *Nature*, 354:82–84.
Levine et al., 1991, *Nature*, 351:453–456.
Lewin, 1990, *Cell*, 61:1161–1164.
Low et al., 1994, *J. Neuroendocrinol.*, 6:285–290.

Maher, 1992, *BioEssays*, 14:807–815.
Markowitz et al., 1988, *J. Virol.*, 62:1120–1124.
McPherson et al., 1991, *PCR: A Practical Approach*, IRL Press.
Miller et al., 1995, *Current Biol.*, 5(9):1047–1056.
Moreadith et al., 1997, *J. Mol. Med.*, 75:208–216.
Morgan et al., 1996, *Proc. Natl. Acad. Sci. USA*, 93:2801–2806.
Mullins et al., 1996, *J. Clinical Investigation*, 98(11, supplement):S37–S40.
Niwa et al., 1993, *J. Biochem.*, 113(3):343–349.
No et al., 1996, *Proc. Natl. Acad. Sci. USA*, 93:3346–3351.
Nussaume et al., 1995, *Mol. Gen. Genet.*, 249:91–101.
O'Banion et al., 1991, *J. Biol. Chem.*, 266:23261–23267.
Odell et al., 1990, *Mol. Gen. Genet.*, 223:369–378.
Orkin et al., 1995, *Report and Recommendation of the Panel to Assess the NIH Investment in Research on Gene Therapy*, Dec. 7, 1995.
Oudet et al., 1978, *Philos. Trans. R. Soc. Lond.*, 283:241–258.
Picksley et al., 1994, *Curr. Opin. Cell. Biol.*, 6:853–858.
Platt et al., 1994, *J. Biol. Chem.*, 269:28558–28562.
Pryciak et al., 1992, *Cell*, 69:769–780.
Ptashne et al., 1990, *Nature*, 346:329–331.
Rao et al., 1996, *J. Cell Biol.*, 135:1441–1455.
Reddy et al., 1991, *J. Virol.*, 65:1507–1515.
Reddy et al., 1992, *Proc. Natl. Acad. Sci. USA*, 89:6721–6725.
Reilly et al., 1990, *DNA and Cell Biol.*, 9(7):535–542.
Rohdewohld et al., 1987, *J. Virol.*, 61:336–343.
Sabbatini et al., 1997, *Cell Growth and Differentiation*, 8:643–653.
Sandmeyer et al., 1990, *Annu Rev. Genet.*, 24:491–518.
Sauer et al., 1990, *Adv. Protein Chem.*, 40:1–61.
Sauer, 1994, *Curr. Opin. Biotechnol.*, 5:521–527.
Sekine et al., 1989, *Proc. Natl. Acad. Sci. USA*, 86:4609–4613.
Shih et al., 1988, *Cell*, 53:531–537.
Skarnes et al., 1992, *Genes & Dev.*, 6:903–918.
Skarnes et al., 1993, *Cur. Opin. Biotech.*, 4:684–689.
Smithies et al., 1985, *Nature*, 317:230–234.
Songyang et al., 1993, *Cell*, 72:767–778.
Theiler. 1989. In: *The House Mouse, Atlas of Embryonic Development*, Springer–Verlag, 148–149.
Thomas et al., 1987, *Cell*, 51:503–512.
Thompson et al., 1989, *Cell*, 5:313–321.
Valentine et al., 1994, *Gastroenterology*, 107:1662–1670.
Varmus, 1988, *Science*, 240:1427–1435.
Vinson et al., 1989, *Science*, 246:911–916.
Voet and Voet. 1995. In: *Biochemistry, $2^{nd}$ Ed.*, John Wiley and Sons, 944–949, 965.
von Melchner, 1989, *J. Virol.*, 63:3227–3233.
von Melchner et al., 1992, *Genes and Dev.*, 6:919–927.
Wang et al., 1995, *Somatic Cell and Mol. Genet.*, 21(6):429–441.
Wilson, 1997, *Clin. Exp. Immunol.*, 107(Suppl. 1):31–32.
Wright et al., 1989, *Cell*, 56:607–617.
Yoshida et al., 1995, *Transgenic Research*, 4:277–287.
Zambrowicz et al., 1997, *Proc. Natl. Acad. Sci. USA*, 94:3789–3794.
Zambrowicz et al., 1998, *Int. J. Dev. Biol.*, 42:1025–1036.

* cited by examiner

Identify Positive Pool

To screen all mouse genes (~100,000) with 5-fold redundancy would require about 50 plates of 96-wells (at 100 clones/well).

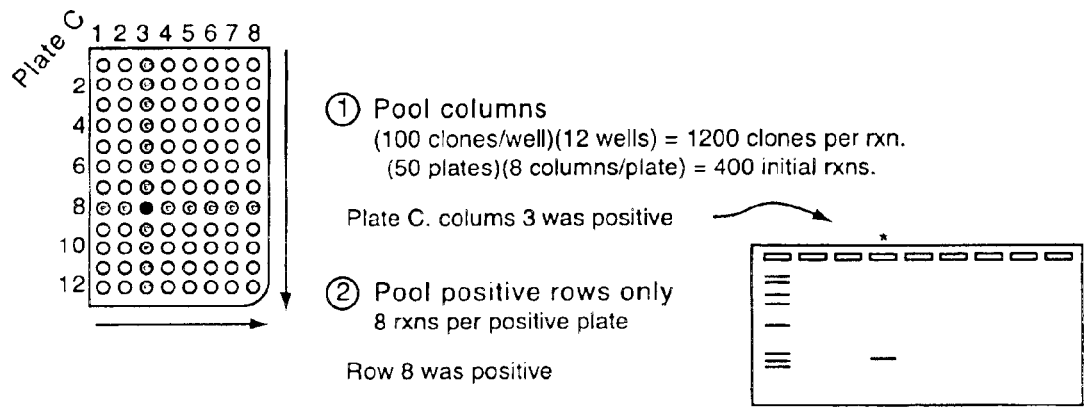

① Pool columns
(100 clones/well)(12 wells) = 1200 clones per rxn.
(50 plates)(8 columns/plate) = 400 initial rxns.

Plate C. colums 3 was positive

② Pool positive rows only
8 rxns per positive plate

Row 8 was positive

Identify Positive Clone

The pool on plate C, column 3, row 8 is thawed and plated as single clones:

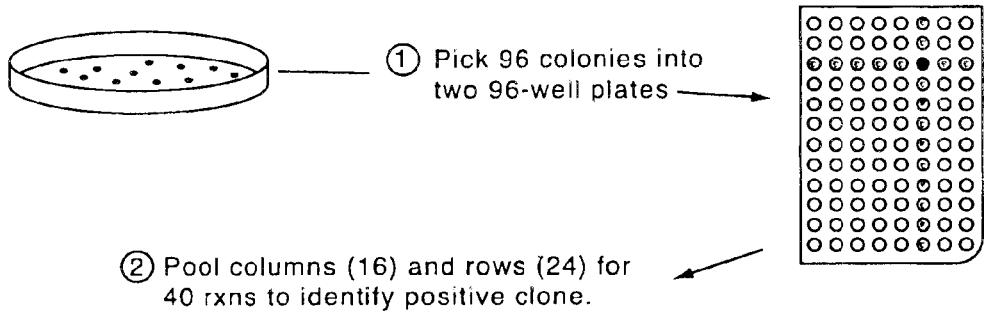

① Pick 96 colonies into two 96-well plates

② Pool columns (16) and rows (24) for 40 rxns to identify positive clone.

FIG. 5

```
OST1 (SEQ ID NO.: 1):              248 TTTATATAATATATTTAATTTGTTTACTCTGGGGTATATATGTGTGAAGAGGACTTCT 302
                                       ||||  ||||||||||||||||||||| |||||||||  ||||||||||||||||||
rat GABA rho3 (SEQ ID NO.: 2):    1547 TTTACATAATATATTTAATTTGTTTACTGGGGTATATGTGTGAAGAGGACTTTT 1601

OST2 (SEQ ID NO.: 3):               56 ACCGTTGCGGAGCGCTCACGTTTCTCAGATAGTACATCAGGTGTCATCGNTGTCAGAAGGT 115
                                       |||||||| ||||  |||||||||||||||||||||||||  | ||||||| |||||||
mouse TCR-ATF1 (SEQ ID NO.: 4):     75 ACCGTTGCGGGGCCCTCACGTTTCTCAGATAGTACATCAGGTGTCATCGTTATCAGAAAGT 134

OST3 (SEQ ID NO.: 5):               58 GIGMHHAGLHERDRKTVEELFXNCKVQVLIATSTLAWGVNFPAHLVIIKGTEYYDGKTRR 237
                                       GIG+HHAGL ++DR   K+Q+LIATSTLAWGVN PAHLVIIKGT+++D K
Yeast ORF G9365 (SEQ ID NO.: 6):  1430 GIGLHHAGLVQKDRSISHQLFQKNRKIQILIATSTLAWGVNLPAHLVIIKGTQFFDAKIEG 1489

OST4 (SEQ ID NO.: 7):              137 GCGCAGAAGTGGTNCTGGAANTTTNTCCGCCNCATCCAGTCTATTAATTGTTGACNGGA 196
seq. from US                           |||||||||||||| |||||| ||| ||| | ||||||||||||||| ||||||| | ||
patent 5470724 (SEQ ID NO.: 8):    166 GCGCAGAAGTGGTCCTGCAACTTTATCCGCCTCCAGTCTATTAATTGTTGCCGGGA 225

OST5 (SEQ ID NO.: 9):              108 TCWIRLGT*RXVGASLEYEYIRAS 179
                                       TCW++L    R VG +L+ +Y  A+
mouse wnt-5A
protein precursor (SEQ ID NO.: 10): 250 TCWLQLADFRKWGDALKEKYDSAA 273

OST6 (SEQ ID NO.: 11):              78 CTTATATGGCTACGGGGCTTCAACATCTCAACATATCCATCACACCAACTACAGCGTGTCCAGGCT 137
human prolyl                           ||||||||||||| ||||||||||||||||||||||||||||||||||||||||| ||||||||
endopeptidase (SEQ ID NO.: 12):   1407 CTTATATGGCTATGGGGCTTCAACATATCCATCACACCAACTACAGTGTTTCCAGGCT 1466

OST7 (SEQ ID NO.: 13):             109 AAGCATGTAGCAGTTGTAGGACACACTAGACGAGAGCACCAGATCTCATTGTGGTGGT 168
mouse                                  |||||||||||||||||||||||||||||||||||||||||||||||||||||||||
45S pre rRNA (SEQ ID NO.: 14):    1604 AAGCATGTAGCAGTTGTAGGACACACTAGACGAGAGCACCAGATCTCATTGTGGTGGT 1663

OST8 (SEQ ID NO.: 15):             161 TGGATGCAGNCTACCACTGTGTGGCTGCCCTATTTTACCTCAGTGCCTCAGTTCTGGAAG 220
                                       ||||||||| |||||||||||||||||||||| ||||||||||||||||||||||||||
rat MAL (SEQ ID NO.: 16):          306 TGGATGCAGCCTACCACTGTGTGGCTGCCCTGTTTTACCTCAGTGCCTCAGTCCTGGAAG 365

OST9 (SEQ ID NO.: 17):             103 ACCTGATTGTTATCGGTGGCCTGCAGAAGTCCAGAAATACAGACCAAAGTCAACCAGTA 162
                                       ||||||||||||||||||||||||||||||||||||| ||||||||||||||||||||
mouse malic enzyme (SEQ ID NO.: 18): 1666 ACCTGATTGTTATCGGTGGCCTGCAGAAGTCCAGAGAATACAGACCAAAGTCAACCAGTA 1725
```

FIG. 6

The following table includes 586 OSTs. OSTs with hit into prodom and GenBank patented sequences have been removed as well as sequence with repetitive elements hits.

| OmniBank | DBIAccession | pvalue | Id. | Sequence Description |
|---|---|---|---|---|
| OST4 | gb\|W09445 | 5.0e-133 | 96% | Mus musculus ma63f02.r1 Soares mouse p3NMF19.5 Mus musculus cDNA clone 315387 5' |
| OST5 | gb\|Y00746 | 2.6e-41 | 95% | Mus musculus Mouse mRNA for retinal cyclic-GMP phosphodiesterase gamma-subunit (GMP-PDE) (EC 3.1.4.17) |
| OST22 | gb\|D88454 | 5.9e-48 | 83% | Mus musculus Mouse mRNA |
| OST25 | gb\|U28168 | 1.0e-42 | 87% | Mus musculus Mus musculus GP106 mRNA, complete cds |
| OST30 | gb\|AA048968 | 1.9e-173 | 98% | Mus musculus mj50b06.r1 Soares mouse embryo NbME13.5 14.5 Mus musculus cDNA clone 479507 5' |
| OST36 | gb\|D29016 | 7.5e-71 | 90% | Mus musculus Mouse mRNA for squalene synthase |
| OST38 | gb\|X53732 | 3.0e-106 | 95% | Mus musculus M. musculus T cell receptor alpha chain variable region (V-alpha) |
| OST41 | gb\|J00360 | 1.8e-70 | 10% | Mus musculus mouse alpha-amylase-2 gene: pancreatic mrna |
| OST42 | gb\|M33190 | 4.0e-34 | 62% | Rattus norvegicus Rat cytochrome P450 II A3 (CYP2A3) gene, complete cds |
| OST45 | gb\|AA003309 | 1.4e-145 | 99% | Mus musculus mg47d10.r1 Soares mouse embryo NbME13.5 14.5 Mus musculus cDNA clone 426931 5' |
| OST51 | gb\|D86214 | 1.5e-45 | 66% | Mus musculus House mouse; Musculus domesticus Postnatal (0 day) Brain mRNA for Ca2+ dependent activator protein for secretion, complete cds |
| OST56 | gb\|AA189233 | 2.6e-37 | 97% | Mus musculus mu52c11.r1 Soares mouse lymph node NbMLN Mus musculus cDNA clone 643028 5' similar to TR:G294850 G294850 ALPHA-MUSCLE ACTIN |
| OST74 | gb\|Y00169 | 7.5e-112 | 89% | Rattus norvegicus Rat TM-4 gene for fibroblast tropomyosin 4 |
| OST75 | gb\|Z72384 | 1.0e-126 | 95% | Mus musculus M. musculus Igk-Vk2 (70/3) gene |
| OST86 | gb\|AA190122 | 1.7e-31 | 88% | Mus musculus mu46f05.r1 Soares mouse lymph node NbMLN Mus musculus cDNA clone 642465 5' |
| OST95 | gb\|AA104745 | 1.8e-178 | 96% | Mus musculus mo56d03 .r1 Life Tech mouse embryo 8 5dpc 10664019 Mus musculus cDNA clone 557573 5' similar to SW:YA36_SCHPO Q09713 HYPOTHETICAL 37.7 KD PROTEIN C18B11.06 IN CHR1 |
| OST98 | gb\|H33806 | 7.3e-40 | 88% | Rattus sp. EST110153 Rattus sp. cDNA 5' end |
| OST117 | gb\|AA156426 | 4.0e-111 | 97% | Homo sapiens z151b07.s1 Soares pregnant uterus NbHPU Homo sapiens cDNA clone 505429 3' similar to TR:G632498 G632498 CLEAVAGE STIMULATION FACTOR 77KDA SUBUNIT |
| OST118 | gb\|D87684 | 8.6e-154 | 84% | Homo sapiens Human mRNA for KIAA0242 gene, partial cds |
| OST119 | gb\|D87077 | 2.0e-145 | 92% | Homo sapiens Human mRNA for KIAA0240 gene, partial cds |
| OST121 | gb\|D28482 | 3.1e-161 | 83% | Homo sapiens Human scr2 mRNA for RNA binding protein SCR2, complete cds |
| OST133 | gb\|AA114106 | 1.2e-52 | 73% | Homo sapiens zn66h09.r1 Stratagene HeLa cell s3 937216 Homo sapiens cDNA clone 563201 5' |
| OST154 | gb\|AA107843 | 4.0e-128 | 82% | Mus musculus mo49c06 .r1 Life Tech mouse embryo 10 5dpc 10665016 Mus musculus cDNA clone 556906 5' similar to gb: J05277 Mouse hexokinase mRNA, complete cds (MOUSE) |
| OST178 | gb\|X05300 | 8.1e-143 | 92% | Rattus norvegicus Rat mRNA for ribophorin 1 |
| OST193 | gb\|C06148 | 4.8e-107 | 84% | Homo sapiens similar to glutamyl-tRNA synthetase |
| OST243 | gb\|H32146 | 4.8e-38 | 86% | Rattus sp. EST106973 Rattus sp. cDNA 5' end similar to Synapsin I |
| OST246 | gb\|AA009152 | 1.8e-81 | 79% | Mus musculus mh01b09.r1 Soares mouse embryo NbME13.5 14.5 Mus musculus cDNA clone 441209 5' |
| OST268 | gb\|M12658 | 1.2e-91 | 93% | Mus musculus Mouse 4.5S RNA gene |
| OST280 | gb\|AA058245 | 1.5e-141 | 94% | Mus musculus mg74e11.r1 Soares mouse embryo NbME13.5 14.5 Mus musculus cDNA clone 438764 5' |

FIG. 8a

| | | | | |
|---|---|---|---|---|
| OST281 | gb|U65313 | 1.8e-180 | 98% | Mus musculus Mus musculus ras-GTPase-activating SH3-domain binding protein (G3BP) gene, complete cds |
| OST295 | gb|AA048390 | 4.2e-60 | 83% | Mus musculus mj29a11.r1 Soares mouse embryo NbME13.5 14.5 Mus musculus cDNA clone 477500 5' similar to gb:J02809 Mouse neutral specific calmodulin-binding protein P-57 mRNA, |
| OST297 | gb|X77585 | 3.0e-168 | 10% | Mus musculus M. musculus mRNA for thioredoxin |
| OST300 | gb|M75122 | 1.8e-203 | 98% | Mus musculus Mouse acid beta-galactosidase (GLB-1) gene, exon 16 |
| OST301 | gb|W34850 | 2.7e-97 | 97% | Mus musculus mc62b02.r1 Soares mouse embryo NbME13.5 14.5 Mus musculus cDNA clone 353067 5' similar to gb:U11248 Mus musculus C57BL/6J ribosomal protein S28 mRNA, complete |
| OST311 | gb|W80427 | 3.0e-73 | 85% | Homo sapeins zd82d06.s1 Soares fetal heart NbHH19W Homo sapiens cDNA clone 347147 3' similar to PIR:A54766 A54766 metastasis-associated protein mta-1 |
| OST314 | gb|T34710 | 4.0e-54 | 73% | Home sapiens EST73642 Homo sapiens cDNA 5' end similar to None |
| OST316 | gb|W11499 | 1.2e-72 | 99% | Mus musculus ma80h02 .r1 Soares mouse p3NMF19.5 Mus musculus CDNA clone 317043 5' similar to SW:UCRX_BOVIN P00130 UBIQUINOL-CYTOCHROME C REDUCTASE 7.2 KD PROTEIN |
| OST328 | gb|W10861 | 3.7e-59 | 89% | Mus musculus ma55c03.r1 Soares mouse p3NMF19.5 Mus musculus CDNA clone 314596 5' |
| OST331 | gb|U17698 | 6.8e-119 | 83% | Mus musculus Mus musculus abiphilin-1 (abi-1) mRNA, complete cds |
| OST342 | gb|U10120 | 3.1e-143 | 95% | Mus musculus Mus musculus SKD2 mRNA, complete cds |
| OST356 | gb|M60456 | 1.8e-117 | 92% | Mus musculus Mouse cyclophilin mRNA, complete cds |
| OST361 | gb|W77360 | 5.7e-37 | 90% | Mus musculus me65f11.r1 Soares mouse embryo NbME13.5 14.5 Mus musculus cDNA clone 400461 5' |
| OST368 | gb|D87662 | 2.9e-184 | 97% | Mus musculus House mouse; Musculus domesticus mRNA for 14-3-3 tau, complete cds |
| OST386 | gb|X99946 | 2.6e-35 | 85% | Mus musculus M. musculus 94kb genomic sequence encoding Tsx gene |
| OST389 | gb|T51727 | 1.8e-78 | 89% | Homo sapiens yb28c11.r1 Home sapiens cDNA clone 72500 5' |
| OST401 | gb|W29220 | 3.1e-33 | 97% | Mus musculus mc19e08.r1 Soares mouse p3NMF19.5 Mus musculus cDNA clone 348998 5' similar to SW:YEFA_ECOLI P32054 GDP-MANNOSE DEHYDRATASE |
| OST413 | gb|N48542 | 2 .0e-68 | 78% | Homo sapiens yy49d07.r1 Homo sapiens cDNA clone 276877 5' |
| OST418 | gb|G21163 | 1.7e-84 | 85% | Homo sapiens human STS WI-15024 |
| OST421 | gb|G25365 | 6.1e-56 | 86% | Homo sapiens human STS EST334292 |
| OST425 | gb|X04480 | 8.1e-58 | 99% | Mus musculus Mouse mRNA for preproinsulin-like growth factor IA |
| OST430 | gb|W97937 | 5.7e-93 | 96% | Mus musculus me73g07.r1 Soares mouse embryo NbME13.5 14.5 Mus musculus cDNA clone 401244 5' similar to gb:M23419 INITIATION FACTOR 5A (HUMAN) |
| OST439 | gb|M26756 | 2.4e-134 | 87% | Mus musculus Mouse malic enzyme mRNA, complete cds |
| OST442 | gb|W25938 | 2.6e-49 | 70% | Homo sapiens 15b8 Human retina cDNA randomly primed sublibrary Homo sapiens cDNA |
| OST448 | gb|Y07569 | 4.3e-72 | 88% | Homo sapiens H. sapiens mRNA for PHAPI2a protein |
| OST531 | gb|X95591 | 3.1e-206 | 91% | Mus musculus M. musculus mRNA for C1D protein |
| OST536 | gb|W75435 | 4.6e-75 | 95% | Mus musculus me50d06.r1 Soares mouse embryo NbME13.5 14.5 Mus musculus cDNA clone 390923 5' similar to gb:U09659 Mus musculus chaperonin 10 mRNA, complete cds (MOUSE) |
| OST542 | gb|W14808 | 6.8e-216 | 99% | Mus musculus mb32g03.r1 Soares mouse p3NMF19.5 Mus musculus cDNA clone 331156 5' similar to SW: YE04_YEAST P32642 HYPOTHETICAL 27.5 KD PROTEIN IN |

FIG. 8b

| | | | | |
|---|---|---|---|---|
| OST562 | gb\|X61433 | 7.6e-68 | 97% | RAD3-BMH1 INTERGENIC REGION. [1] Mus musculus M. musculus mRNA for sodium/potassium ATPase beta subunit |
| OST568 | gb\|AA007930 | 1.5e-31 | 67% | Mus musculus mg64a07.r1 Soares mouse embryo NbMe13.5 14.5 Mus musculus cDNA clone 437748 5' |
| OST571 | gb\|AA111278 | 2.1e-147 | 92% | Mus musculus mo53f02.r1 Life Tech mouse embryo 10 5dpc 10665016 Mus musculus cDNA clone 557307 5' |
| OST572 | gb\|AA130347 | 1.2e-103 | 85% | Homo sapiens zo05g10.s1 Stratagene endothelial cell 937223 Homo sapiens cDNA clone 566850 3' |
| OST573 | gb\|L42855 | 4.0e-69 | 75% | Rattus norvegicus Rattus norvegicus RNA polymerase II transcription factor SIII P18 subunit mRNA, complete cds |
| OST577 | gb\|AA020459 | 2.1e-91 | 92% | Mus musculus mh61a06.r1 Soares mouse placenta 4NbMP13.5 14.5 Mus musculus cDNA clone 455410 5' |
| OST581 | gb\|R96552 | 2.0e-90 | 80% | Homo sapiens yq54e02.r1 Homo sapiens cDNA clone 199610 5' |
| OST582 | gb\|D17695 | 1.9e-218 | 91% | Rattus rattus Rat mRNA for water channel aquaporin 3 (AQP3), complete cds |
| OST591 | gb\|L43326 | 3.6e-103 | 85% | Mus musculus Mus musculus domesticus coiled-coil protein (CG-1) mRNA, complete cds |
| OST593 | gb\|W70777 | 3.4e-117 | 98% | Mus musculus me44a02.r1 Soares mouse embryo NbME13.5 14.5 Mus musculus cDNA clone 390314 5' |
| OST594 | gb\|X94616 | 2.6e-142 | 87% | Mus musculus M. musculus mRNA for glycogen synthase |
| OST595 | gb\|U67137 | 7.0e-51 | 86% | Rattus norvegicus Rattus norvegicus PSD-95/SAP90-associated protein-1 mRNA, complete cds |
| OST598 | gb\|X53476 | 2.2e-235 | 98% | Mus musculus Mouse mRNA for non-histone chromosomal protein HMG-14 |
| OST600 | gb\|U70494 | 1.0e-188 | 96% | Mus musculus Mus musculus histone H2A.Z (H2A.Z) mRNA, complete cds |
| OST607 | gb\|W55702 | 1.2e-71 | 85% | Mus musculus ma35d03.r1 Life Tech mouse brain Mus musculus cDNA clone 312677 5' |
| OST613 | gb\|AA184809 | 9.8e-68 | 97% | Mus musculus mu45h05.r1 Soares mouse lymph node NbMLN Mus musculus cDNA clone 642393 5' similar to gb:L00993 Mus musculus autoantigen La (MOUSE) |
| OST618 | gb\|H11817 | 1.5e-95 | 86% | Homo sapiens ym11f07.r1 Homo sapiens cDNA clone 47592 5' |
| OST620 | gb\|AA117282 | 1.0e-78 | 83% | Mus musculus mn25a10.r1 Beddington mouse embryonic region Mus musculus cDNA clone 538938 5' similar to gb: L35599 Mus musculus Y-box binding protein mRNA, 3' end (MOUSE) |
| OST623 | gb\|AA001326 | 5.7e-106 | 81% | Homo sapiens zh83b02.r1 Soares fetal liver spleen 1NFLS S1 Homo sapiens cDNA clone 427851 5' |
| OST626 | gb\|D83768 | 1.4e-47 | 81% | Homo sapiens Human clone N9S Rep-8 mRNA, partial cds |
| OST663 | gb\|AA028410 | 3.2e-114 | 88% | Mus musculus mil9a06.r1 Soares mouse p3NMF19.5 Mus musculus cDNA clone 463954 5' similar to gb:M18775 Mouse tau microtubule binding protein mRNA, complete (MOUSE) |
| OST664 | gb\|U11027 | 2.6e-106 | 87% | Mus musculus Mus musculus C57BL/6J Sec61 protein complex gamma subunit mRNA, complete cds |
| OST671 | gb\|S64860 | 8.4e-211 | 95% | Mus sp. NonO=non-POU domain-containing octamer-binding protein [mice, B-cell leukemia, BCL1, mRNA, 2411 nt] |
| OST679 | gb\|W14516 | 9.9e-139 | 95% | Mus musculus mb24h01.r1 Soares mouse p3NMF19.5 Mus musculus cDNA clone 330385 5' |
| OST680 | gb\|L20258 | 4.2e-232 | 95% | Mus musculus Mouse stathmin gene |
| OST702 | gb\|M78893 | 5.7e-52 | 85% | Homo sapiens EST01041 Homo sapiens cDNA clone HHCPB34 similar to cAMP-regulated phosphoprotein |
| OST707 | gb\|H19122 | 1.2e-85 | 82% | Homo sapiens ym44d11.r1 Homo sapiens cDNA clone 51237 5' |
| OST716 | gb\|W62791 | 4.5e-74 | 96% | Mus musculus md86e09.r1 Soares mouse embryo NbME13.5 14.5 Mus musculus cDNA clone 375304 5' |

FIG. 8c

| | | | | |
|---|---|---|---|---|
| | | | | (Cx31.1) mRNA, complete cds |
| OST1096 | gbID87077 | 7.7e-112 | 88% | Homo sapiens Human mRNA for KIAA0240 gene, partial cds |
| OST1105 | gbIW44423 | 1.0e-66 | 86% | Homo sapiens zc28f04.s1 Soares senescent fibroblasts NbHSF Homo sapiens cDNA clone 323647 3' |
| OST1116 | gbIX62249 | 3.1e-36 | 80% | Mus musculus M. musculus scRNA |
| OST1137 | gbIM63485 | 1.2e-89 | 94% | Rattus norvegicus Rat matrin 3 mRNA |
| OST1145 | gbIX80040 | 1.4e-128 | 91% | Mus musculus M. musculus Hesx1 mRNA |
| OST1152 | gbIW79970 | 6.4e-109 | 10% | Mus musculus me90d10.r1 Soares mouse embryo NbME13.5 14.5 Mus musculus cDNA clone 402835 5' similar to gb:X57351 INTERFERON-INDUCIBLE PROTEIN 1-8D |
| OST1155 | gbIW10324 | 2.3e-65 | 95% | Mus musculus me42d11.r1 Soares mouse p3NMF19.5 Mus musculus cDNA clone 313365 5' similar to gb:M29844 APOLIPOPROTEIN C-II PRECURSOR |
| OST1165 | gbIW54649 | 1.9e-184 | 97% | Mus musculus md07b12.r1 Soares mouse embryo NbME13.5 14.5 Mus musculus cDNA clone 367679 5' |
| OST1179 | gbIAA008986 | 8.5e-84 | 94% | Mus musculus mg99e02.r1 Soares mouse embryo NbME13.5 14.5 Mus musculus cDNA clone 441146 5' |
| OST1186 | gbIU89840 | 2.8e-70 | 96% | Mus musculus Mus musculus prostate secretory protein (PSP94) mRNA, complete cds |
| OST1192 | gbIW82490 | 5.3e-127 | 96% | Mus musculus mf04e04.r1 Soares mouse p3NMF19.5 Mus musculus cDNA clone 404094 5' |
| OST1207 | gbIAA063763 | 1.3e-56 | 86% | Mus musculus mj79d10.r1 Soares mouse p3NMF19.5 Mus musculus cDNA clone 482323 5' |
| OST1223 | gbIAA002931 | 1.5e-189 | 99% | Mus musculus mg40f08.r1 Soares mouse embryo NbME13.5 14.5 Mus musculus cDNA clone 426279 5' |
| OST1226 | gbIU37353 | 7.5e-279 | 95% | Mus musculus Mus musculus protein phosphatase 2A B' alpha3 regulatory subunit mRNA, partial cds |
| OST1233 | gbIW98701 | 6.3e-91 | 98% | Mus musculus mg12f05.r1 Soares mouse embryo NbME13.5 14.5 Mus musculus cDNA clone 423585 5' |
| OST1234 | gbID85904 | 1.1e-180 | 98% | Mus musculus Mouse mRNA for apg-2, complete cds |
| OST1241 | gbIU09850 | 4.8e-184 | 92% | Homo sapiens Human zinc finger protein (ZNF143) mRNA, complete cds |
| OST1247 | gbIAA051266 | 4.7e-126 | 97% | Mus musculus mj43h02.r1 Soares mouse embryo NbME13.5 14.5 Mus musculus cDNA clone 478899 5' similar to SW:L10K_RAT Q05310 LEYDIG CELL TUMOR 10 KD PROTEIN |
| OST1265 | gbIX96973 | 6.8e-183 | 96% | Mus musculus M. musculus mRNA for Lasp-1 protein |
| OST1267 | gbIR84271 | 1.6e-32 | 86% | Homo sapiens yq22g02.r1 Soares retina N2b4HR Homo sapiens cDNA clone 274730 5' similar to SP: YPK1_YEAST P12688 SERINE/THREONINE-PROTEIN KINASE YPK1 |
| OST1269 | gbIU19977 | 4.0e-130 | 84% | Homo sapiens Human preprocarboxypeptidase A2 (proCPA2) mRNA, complete cds |
| OST1274 | gbIM14634 | 2.1e-139 | 85% | Rattus norvegicus Rat mitochondrial propionyl-CoA carboxylase (PCCase) beta-subunit mRNA, complete cds |
| OST1294 | gbIJ03583 | 6.8e-69 | 95% | Rattus norvegicus Rat clathrin heavy chain mRNA, complete cds |
| OST1339 | gbIM97190 | 3.1e-118 | 83% | Homo sapiens Human Sp2 protein mRNA complete cds |
| OST1341 | gbIW89611 | 7.8e-142 | 93% | Mus musculus mf72h02.r1 Soares mouse embryo NbME13.5 14.5 Mus musculus cDNA clone 419859 5' |
| OST1354 | gbIW74481 | 2.2e-64 | 85% | Homo sapiens zd75b12.s1 Soares fetal heart NbHH19W Homo sapiens cDNA clone 346463 3' |
| OST1359 | gbIW65672 | 5.1e-35 | 95% | Mus musculus me13d09.r1 Soares mouse embryo NbME13.5 14.5 Mus musculus cDNA clone 387377 5' similar to SW:UBC5_DROME P35128 UBIQUITIN-CONJUGATING ENZYME E2-17 KD |
| OST1369 | gbIW62550 | 1.1e-109 | 97% | Mus musculus md73e11.r1 Soares mouse embryo NbME13.5 14.5 Mus musculus cDNA clone 374060 5' similar to gb:L06039 Mouse platelet endothelial cell |

FIG. 8d

| | | | | |
|---|---|---|---|---|
| | | | | adhesion molecule 1 |
| OST1376 | gb\|X63615 | 1.1e-33 | 92% | Mus musculus M. musculus Camk-2 mRNA for Ca2+/calmodulin dependent protein kinase II beta subunit |
| OST1387 | gb\|C15521 | 6.5e-57 | 93% | Homo sapiens Human fetal brain cDNA 5'-end GEN-149C01 |
| OST1410 | gb\|W59607 | 4.8e-77 | 89% | Mus musculus md73a06.r1 Soares mouse embryo NbME13.5 14.5 Mus musculus cDNA clone 374002 5' |
| OST1419 | gb\|W10923 | 1.2e-122 | 97% | Mus musculus ma40a11.r1 Soares mouse p3NMF19.5 Mus musculus cDNA clone 313148 5' |
| OST1432 | gb\|W89889 | 1.7e-145 | 94% | Mus musculus mf77f07.r1 Soares mouse embryo NbME13.5 14.5 Mus musculus cDNA clone 420325 5' |
| OST1453 | gb\|C18312 | 5.6e-92 | 86% | Homo sapiens Human placenta cDNA 5'-end GEN-560D09 |
| OST1457 | gb\|R78851 | 5.9e-45 | 80% | Homo sapiens yi90f03.r1 Homo sapiens cDNA clone 146525 5' |
| OST1470 | gb\|J05504 | 1.5e-136 | 95% | Mus musculus Mouse guanylate cyclase/atrial natriuretic factor receptor mRNA, complete cds |
| OST1478 | gb\|U57821 | 8.4e-55 | 80% | Mus musculus Mus musculus inhibitor of MyoD family-b (I-mf) mRNA, complete cds |
| OST1488 | gb\|U24681 | 4.3e-235 | 94% | synthetic construct Synthetic NAHD: cytochrome c reductase fusion protein mRNA, complete cds |
| OST1492 | gb\|W10703 | 3.6e-109 | 98% | Mus musculus ma53g05.r1 Soares mouse p3NMF19.5 Mus musculus cDNA clone 314456 5' |
| OST1493 | gb\|AA097483 | 3.5e-197 | 98% | Mus musculus mk17d04.r1 Soares mouse p3NMF19.5 Mus musculus cDNA clone 493159 5' similar to gb:L05093 60S RIBOSOMAL PROTEIN L18A (HUMAN) |
| OST1499 | gb\|T51184 | 1.3e-60 | 94% | Homo sapiens yb94h05.r1 Homo sapiens cDNA clone 78873 5' |
| OST1504 | gb\|L34260 | 1.7e-196 | 91% | Mus musculus Mus musculus integral membrane protein 1 (Itm1) mRNA, complete cds |
| OST1508 | gb\|L03306 | 1.8e-164 | 94% | Mus musculus Mus musculus core-binding factor mRNA sequence |
| OST1520 | gb\|W18420 | 4.7e-37 | 88% | Mus musculus mb68e07.r1 Soares mouse p3NMF19.5 Mus musculus cDNA clone 334596 5' similar to PIR:JH0457 JH0457 80K nuclear protein - human |
| OST1523 | gb\|U23769 | 7.2e-195 | 92% | Rattus norvegicus Rattus norvegicus CLP36 (clp36) mRNA, complete cds |
| OST1554 | gb\|W85270 | 2.3e-168 | 96% | Mus musculus mf42d05.r1 Soares mouse embryo NbME13.5 14.5 Mus musculus cDNA clone 407721 5' similar to SW:IPYR_BOVIN P37980 INORGANIC PYROPHOSPHATASE |
| OST1556 | gb\|AA117514 | 9.7e-150 | 89% | Mus musculus mn29c09.r1 Beddington mouse embryonic region Mus musculus cDNA clone 539344 5' |
| OST1558 | gb\|H33765 | 2.2e-67 | 86% | Rattus sp. EST110085 Rattus sp. cDNA 5' end |
| OST1567 | gb\|U14636 | 1.7e-39 | 94% | Mus musculus Mus musculus serine/threonine protein kinase DLK mRNA, complete cds |
| OST1601 | gb\|W39611 | 1.3e-89 | 85% | Homo sapiens zc19e08.r1 Soares parathyroid tumor NbHPA Homo sapiens cDNA clone 322790 5' |
| OST1603 | gb\|W09922 | 4.0e-109 | 86% | Mus musculus ma67e08.r1 Soares mouse p3NMF19.5 Mus musculus cDNA clone 315782 5' similar to PIR:S48566 S48566 hypothetical protein L8167.23 - yeast |
| OST1628 | gb\|U51239 | 7.9e-78 | 93% | Mus musculus Mus musculus lysosomal-associated multitransmembrane protein (LAPTm5) mRNA, complete cds |
| OST1649 | gb\|AA049090 | 7.9e-158 | 96% | Mus musculus mj46e07.r1 Soares mouse embryo NbME13.5 14.5 Mus musculus cDNA clone 479172 5' |
| OST1653 | gb\|AA030795 | 5.1e-143 | 97% | Mus musculus mi27f12.r1 Soares mouse embryo NbME13.5 14.5 Mus musculus cDNA clone 464783 5' |
| OST1658 | gb\|W12941 | 5.2e-95 | 97% | Mus musculus ma89d07.r1 Soares mouse p3NMF19.5 Mus musculus cDNA clone |

FIG. 8e

| | | | | |
|---|---|---|---|---|
| OST2110 | gb\|AA051277 | 6.5e-138 | 97% | Mus musculus mj43h08.r1 Soares mouse embryo NbME13.5 14.5 Mus musculus cDNA clone 478911 5' similar to gb:Y00764 UBIQUINOL-CYTOCHROME C REDUCTASE 11 KD PROTEIN (HUMAN) |
| OST2112 | gb\|W85170 | 4.7e-118 | 96% | Mus musculus mf43f03.r1 Soares mouse embryo NbME13.5 14.5 Mus musculus cDNA clone 407837 5' similar to gb:K00558 TUBULIN ALPHA-1 CHAIN (HUMAN) gb:M13441 Mouse alpha-tubulin isotype M-alpha-6 mRNA, complete cds |
| OST2116 | gb\|X76453 | 2.4e-66 | 86% | Rattus norvegicus R. norvegicus (Sprague Dawley) H-rev107 mRNA |
| OST2126 | gb\|W99867 | 1.8e-35 | 85% | Mus musculus mg30b02.r1 Soares mouse embryo NbME13.5 14.5 Mus musculus cDNA clone 425259 5' |
| OST2134 | gb\|W14081 | 5.2e-109 | 98% | Mus musculus ma64g01.r1 Soares mouse p3NMF19.5 Mus musculus cDNA clone 315504 5' similar to PIR:S50866 S50866 4E-BP1 protein-human |
| OST2141 | gb\|H91351 | 3.8e-40 | 79% | Homo sapiens yu87c07.r1 Homo sapiens cDNA clone 240780 5' |
| OST2165 | gb\|W64236 | 1.7e-144 | 93% | Mus musculus md95a11.r1 Soares mouse embryo NbME13.5 14.5 Mus musculus cDNA clone 385724 5' |
| OST2174 | gb\|U85055 | 1.1e-67 | 93% | Mus musculus Mus musculus rap1/rap2 interacting protein mRNA, complete cds |
| OST2177 | gb\|W99250 | 1.9e-122 | 86% | Mus musculus mf60h04.r1 Soares mouse embryo NbME13.5 14.5 Mus musculus cDNA clone 418711 5' |
| OST2182 | gb\|S79780 | 1.4e-55 | 93% | Mus sp. DP-3=protein in regulating cell cycle transcription factor DRTF1/E2F [mice, pl-2, F9 EC, mRNA, 1380 nt] |
| OST2188 | gb\|W10048 | 2.3e-86 | 97% | Mus musculus ma67b07.r1 Soares mouse p3NMF19.5 Mus musculus cDNA clone 315733 5' similar to gb:L02547 CLEAVAGE STIMULATION FACTOR, 50 KD SUBUNIT (HUMAN) |
| OST2191 | gb\|U46854 | 5.4e-61 | 95% | Mus musculus Mus musculus ShcC mRNA, complete cds |
| OST2198 | gb\|T25302 | 3.1e-33 | 69% | Homo sapiens EST039R Homo sapiens cDNA clone BL29-39R |
| OST2218 | gb\|W38136 | 4.1e-112 | 97% | Homo sapiens zc14a11.s1 Soares parathyroid tumor NbHPA Homo sapiens cDNA clone 322268 3' |
| OST2220 | gb\|AA049140 | 6.0e-153 | 93% | Mus musculus mj49c04.r1 Soares mouse embryo NbME13.5 14.5 Mus musculus cDNA clone 479430 5' similar to SW:SYB_TORCA P13701 SYNAPTOBREVIN |
| OST2229 | gb\|AA014563 | 2.8e-109 | 94% | Mus musculus mi67c05.r1 Soares mouse embryo NbME13.5 14.5 Mus musculus cDNA clone 468584 5' |
| OST2236 | gb\|S63758 | 2.4e-93 | 96% | Mus sp. metallothionein-I gene transcription activator [mice, L cells, mRNA, 509 nt] |
| OST2237 | gb\|AA002285 | 1.7e-33 | 10% | Mus musculus mg42c06.r1 Soares mouse embryo NbME13.5 14.5 Mus musculus cDNA clone 426442 5' similar to SW:YB81_YEAST P38326 HYPOTHETICAL 34.3 KD PROTEIN IN PDB1-ABD1 INTERGENIC REGION. [1] |
| OST2250 | gb\|W71063 | 2.0e-137 | 96% | Mus musculus me31e02.r1 Soares mouse embryo NbME13.5 14.5 Mus musculus cDNA clone 389114 5' |
| OST2269 | gb\|U46027 | 3.1e-119 | 94% | Mus musculus Mus musculus CREB transcription factor, novel spliced form, mRNA, partial cds |
| OST2273 | gb\|U33005 | 9.9e-111 | 94% | Mus musculus Mus musculus tbc1 mRNA, complete cds |
| OST2275 | gb\|W30226 | 1.7e-114 | 95% | Mus musculus mc25h04.r1 Soares mouse p3NMF19.5 Mus musculus cDNA clone 349591 5' similar to SW:CICP_BOVIN p35526 CHLORINE CHANNEL PROTEIN P64. |
| OST2285 | gb\|W33930 | 1.2e-43 | 92% | Mus musculus mb54c08.r1 Soares mouse p3NMF19.5 Mus musculus cDNA clone 333230 5' similar to gb:D13315 LACTOYLGLUTATHIONE LYASE (HUMAN) |
| OST2286 | gb\|W82037 | 8.3e-85 | 96% | Mus musculus me94d11.r1 Soares mouse embryo NbME13.5 14.5 Mus musculus cDNA clone 403221 5' similar to |

FIG. 8f

| | | | | |
|---|---|---|---|---|
| OST2297 | gb\|F07734 | 7.8e-34 | 86% | SW:YA9E_SCHPO Q09790 HYPOTHETICAL 23.7 KD PROTEIN C13G6.14 IN CHROMOSOME I. Homo sapiens H. sapiens partial cDNA sequence; clone c-2gb07 |
| OST2307 | gb\|X61399 | 7.0e-66 | 92% | Mus musculus Mouse F52 mRNA for a novel protein |
| OST2321 | gb\|AA100747 | 5.1e-85 | 78% | Homo sapiens zi91h04.r1 Stratagene colon (#937204) Homo sapiens cDNA clone 512023 5' |
| OST2322 | gb\|J02811 | 1.2e-81 | 92% | Rattus sp. Rat myoadenylate deaminase (AMP deaminase) mRNA, complete cds |
| OST2346 | gb\|AB000893 | 1.5e-95 | 94% | Mus musculus Mouse mRNA for synaptotagmin 3, complete cds |
| OST2347 | gb\|D17653 | 2.5e-101 | 85% | Mus musculus Mouse mRNA for HBp15/L22, complete cds |
| OST2353 | gb\|T80097 | 7.4e-73 | 85% | Homo sapiens yd04g12.r1 Homo sapiens cDNA clone 24692 5' |
| OST2357 | gb\|W30066 | 4.1e-133 | 99% | Mus musculus mc23a09.r1 Soares mouse p3NMF19.5 Mus musculus cDNA clone 349336 5' |
| OST2361 | gb\|W18873 | 7.5e-58 | 95% | Mus musculus mc04d04.r1 Soares mouse p3NMF19.5 Mus musculus cDNA clone 337927 5' |
| OST2367 | gb\|X97831 | 1.9e-104 | 85% | Rattus norvegicus R. norvegicus mRNA for carnitine/acylcarnitine carrier protein |
| OST2368 | gb\|AA013837 | 6.1e-32 | 77% | Mus musculus mh24c06.r1 Soares mouse placenta 4NbMP13.5 14.5 Mus musculus cDNA clone 443434 5' |
| OST2379 | gb\|L10911 | 1.2e-105 | 91% | Homo sapiens Homo sapiens splicing factor (CC1.4) mRNA, complete cds |
| OST2380 | gb\|W87091 | 9.5e-88 | 90% | Mus musculus mf58d10.r1 Soares mouse embryo NbME13.5 14.5 Mus musculus cDNA clone 418483 5' |
| OST2381 | gb\|AA080090 | 8.3e-126 | 96% | Mus musculus mj98h06.r1 Soares mouse p3NMF19.5 Mus musculus cDNA clone 484187 5' |
| OST2382 | gb\|AA015380 | 5.1e-126 | 92% | Mus musculus mg94g12.r1 Soares mouse embryo NbME13.5 14.5 Mus musculus cDNA clone 440710 5' similar to gb:M31690 Mouse argininosuccinate synthetase |
| OST2389 | gb\|U85614 | 2.0e-59 | 91% | Mus musculus Mus musculus SRG3 mRNA, complete cds |
| OST2395 | gb\|AA122609 | 5.0e-138 | 10% | Mus musculus mn25h06.r1 Beddington mouse embryonic region Mus musculus cDNA clone 539003 5' |
| OST2400 | gb\|W34469 | 4.2e-122 | 86% | Mus musculus ma98e09.r1 Soares mouse p3NMF19.5 Mus musculus cDNA clone 318760 5' |
| OST2401 | gb\|AA049859 | 3.7e-83 | 91% | Mus musculus mj13d01.r1 Soares mouse embryo NbME13.5 14.5 Mus musculus cDNA clone 475969 5' similar to SW:YAQ6_SCHPO Q10106 HYPOTHETICAL 29.7 KD PROTEIN C18G6.06 IN CHROMOSOME I. |
| OST2416 | gb\|W14179 | 3.1e-54 | 94% | Mus musculus mb38b08.r1 Soares mouse p3NMF19.5 Mus musculus cDNA clone 331671 5' |
| OST2418 | gb\|N25844 | 1.3e-47 | 81% | Homo sapiens yx22f02.r1 Homo sapiens cDNA clone 262491 5' |
| OST2433 | gb\|AA104747 | 2.4e-164 | 97% | Mus musculus mo56e01.r1 Life Tech mouse embryo 8 5dpc 10664019 Mus musculus cDNA clone 557592 5' similar to gb: M31642 HYPOXANTHINE-GUANINE PHOSPHORIBOSYLTRANSFERASE (HUMAN); gb: J00423 mouse hypoxanthine phosphoribosyltransferase (hprt) mrna |
| OST2442 | gb\|W35819 | 1.7e-55 | 91% | Mus musculus mc14g04.r1 Soares mouse p3NMF19.5 Mus musculus cDNA clone 348534 5' |
| OST2447 | gb\|AA061741 | 1.0e-58 | 94% | Mus musculus mj90b07.r1 Soares mouse p3NMF19.5 Mus musculus cDNA clone 483349 5' similar to WP:C32A3.3 CE05343 COILED COIL DOMAINS |
| OST2455 | gb\|AA167801 | 4.2e-62 | 90% | Homo sapiens zq38c06.r1 Stratagene hNT neuron (#937233) Homo sapiens cDNA clone 631978 5' |
| OST2459 | gb\|U05333 | 3.4e-119 | 96% | Mus musculus Mus musculus co-chaperonin 'cofactor A' mRNA, complete cds |
| OST2464 | gb\|W85263 | 1.8e-116 | 94% | Mus musculus mf45h09.r1 Soares mouse |

FIG. 8g

| | | | | |
|---|---|---|---|---|
| OST2829 | gb\|AA002649 | 7.7e-90 | 94% | LPS-binding protein Mus musculus mg38g06.r1 Soares mouse embryo NbME13.5 14.5 Mus musculus cDNA clone 426106 5' similar to SW:MSE5_HUMAN Q00587 SERUM PROTEIN MSE55. [1] |
| OST2834 | gb\|U57692 | 1.4e-222 | 97% | Mus musculus Mus musculus N-terminal asparagine amidohydrolase (Ntan1) mRNA, complete cds |
| OST2835 | gb\|AA060795 | 2.1e-89 | 97% | Mus musculus mj79d05.r1 Soares mouse p3NMF19.5 Mus musculus cDNA clone 482313 5' similar to WP:F42H10.4 CE00166 CRIP |
| OST2839 | gb\|AA163971 | 6.0e-61 | 70% | Mus musculus ms40a01.r1 Life Tech mouse embryo 13 5dpc 10666014 Mus musculus cDNA clone 613992 5' |
| OST2842 | gb\|W54515 | 6.1e-64 | 91% | Mus musculus md09a10.r1 Soares mouse embryo NbME13.5 14.5 Mus musculus cDNA clone 367866 5' similar to gb:U07151 ADP-RIBOSYLATION FACTOR-LIKE PROTEIN 3 |
| OST2877 | gb\|J03583 | 1.3e-66 | 93% | Rattus norvegicus Rat clathrin heavy chain nRNA, complete cds |
| OST2883 | gb\|W34850 | 4.8e-75 | 93% | Mus musculus mc62b02.r1 Soares mouse embryo NbME13.5 14.5 Mus musculus cDNA clone 353067 5' similar to gb:U11248 Mus musculus C57BL/6J ribosomal protein S28 mRNA, complete (MOUSE) |
| OST2892 | gb\|W97758 | 1.4e-125 | 98% | Mus musculus mg01e10.r1 Soares mouse embryo NbME13.5 14.5 Mus musculus cDNA clone 422538 5' similar to gb:J04823_rna1 CYTOCHROME C OXIDASE POLYPEPTIDE VIII-LIVER/HEART |
| OST2897 | gb\|W11047 | 7.9e-132 | 97% | Mus musculus ma78d10.r1 Soares mouse P3NMF19.5 Mus musculus cDNA clone 316819 5' |
| OST2909 | gb\|AA166258 | 8.9e-120 | 96% | Mus musculus ms49c09.r1 Life Tech mouse embryo 13 5dpc 10666014 Mus musculus cDNA clone 614896 5' |
| OST2911 | gb\|U73478 | 1.4e-117 | 86% | Mus musculus Mus musculus acidic nuclear phosphoprotein pp32 mRNA, complete cds |
| OST2914 | gb\|U12236 | 4.0e-136 | 95% | Mus musculus Mus musculus AKR alpha M290 integrin mRNA, complete cds |
| OST2916 | gb\|D77002 | 1.4e-67 | 92% | Mus musculus Mouse embryonal carcinoma F9 cell cDNA, 93E10 |
| OST2921 | gb\|W75740 | 8.4e-106 | 98% | Mus musculus me55b06.r1 Soares mouse embryo NbME13.5 14.5 Mus musculus cDNA clone 391379 5' |
| OST2922 | gb\|D50544 | 8.4e-135 | 88% | Homo sapiens Human lymphocyte mRNA for TFIID subunit p22, complete cds |
| OST2923 | gb\|W85631 | 3.2e-108 | 97% | Mus musculus mf37b01.r1 Soares mouse embryo NbME13.5 14.5 Mus musculus cDNA clone 407209 5' |
| OST2926 | gb\|W59561 | 6.3e-164 | 94% | Mus musculus md72g01.r1 Soares mouse embryo NbME13.5 14.5 Mus musculus cDNA clone 373968 5' |
| OST2929 | gb\|W75735 | 3.0e-92 | 92% | Mus musculus me50h12.r1 Soares mouse embryo NbME13.5 14.5 Mus musculus cDNA clone 390983 5' |
| OST2934 | gb\|M82904 | 1.8e-75 | 93% | Mus musculus Mouse myotonic dystrophy region mRNA |
| OST2940 | gb\|AA154635 | 1.4e-114 | 97% | Mus musculus mn44c11.r1 Beddington mouse embryonic region Mus musculus cDNA clone 540788 5' similar to gb:X83590 M. musculus mRNA for ribosomal protein L5, 3' end |
| OST2942 | gb\|W34882 | 1.4e-91 | 96% | Mus musculus mc40a05.r1 Soares mouse p3NMF19.5 Mus musculus cDNA clone 350960 5' |
| OST2948 | gb\|AA108292 | 5.1e-32 | 81% | Rattus norvegicus EST0035 rat lambda ZAPII library (C.P. Hamel) Rattus norvegicus cDNA clone pC093 5' similar to ADP-ribosylation factor (ARF)-like protein |
| OST2953 | gb\|W10606 | 1.8e-97 | 98% | Mus musculus ma44d11.r1 Soares mouse p3NMF19.5 Mus musculus cDNA clone 313557 5' similar to PIR:JS0738 JS0738 ATPase inhibitor protein precursor, mitochondrial - rat [1] |
| OST2956 | gb\|AA049172 | 3.1e-137 | 97% | Mus musculus mj46d07.r1 Soares mouse |

FIG. 8h

| | | | | |
|---|---|---|---|---|
| | | | | embryo NbME13.5 14.5 Mus musculus cDNA clone 479149 5' similar to WP:F45E12.4 CE02740 |
| OST2963 | gb\|W04744 | 4.2e-31 | 80% | Homo sapiens za79c08.r1 Soares fetal lung NbHL19W Homo sapiens cDNA clone 298766 5' |
| OST2971 | gb\|AA120487 | 9.2e-107 | 10% | Mus musculus mn12f07.r1 Beddington mouse embryonic region Mus musculus cDNA clone 537733 5' similar to SW:YBN5_YEAST P38219 HYPOTHETICAL 44.2 KD PROTEIN IN SCO2-MRF1 INTERGENIC REGION. |
| OST2974 | gb\|U33553 | 2.6e-102 | 88% | Rattus norvegicus Rattus norvegicus neuroglycan C precursor mRNA, complete cds |
| OST2977 | gb\|X97755 | 6.1e-164 | 97% | Mus musculus M. musculus mRNA MSI |
| OST2981 | gb\|AA206420 | 1.2e-71 | 85% | Homo sapiens zq51b02.s1 Stratagene neuroepithelium (#937231) Homo sapiens cDNA clone 645099 3' similar to TR:G972006 G972006 MRNA; EXPRESSED SEQUENCE TAG |
| OST2983 | gb\|W49206 | 1.8e-119 | 98% | Mus musculus mc91g12.r1 Soares mouse embryo NbME13.5 14.5 Mus musculus cDNA clone 355942 5' similar to PIR:S44900 S44900 ZK652.10 protein Caenorhabditis elegans |
| OST2987 | gb\|AA027683 | 2.3e-134 | 96% | Mus musculus ml12b01.r1 Soares mouse p3NMF19.5 Mus musculus cDNA clone 463273 5' |
| OST2988 | gb\|X52129 | 2.2e-52 | 73% | Mus musculus domesticus Mouse testis-specific mRNA pBs6.2 |
| OST2989 | gb\|AA152050 | 1.3e-46 | 78% | Homo sapiens zl48b12.r1 Soares pregnant uterus NbHPU Homo sapiens cDNA clone 505151 5' similar to gb:M90356_cds1 TRANSCRIPTION FACTOR BTF3 (HUMAN) |
| OST2991 | gb\|AA003171 | 8.4e-151 | 93% | Mus musculus mg56h09.r1 Soares mouse embryo NbME13.5 14.5 Mus musculus cDNA clone 437057 5' similar to gb:M24194 GUANINE NUCLEOTIDE-BINDING PROTEIN BETA SUBUNIT-LIKE PROTEIN (HUMAN); gb:X75313 M. musculus |
| OST2994 | gb\|R51546 | 1.9e-51 | 83% | Homo sapiens yg72h12.r1 Homo sapiens cDNA clone 38905 5' similar to SP:VIL1_CHICK P02640 |
| OST2996 | gb\|X99921 | 1.6e-82 | 10% | Mus musculus M. musculus mRNA for S100 calcium-binding protein A13 |
| OST2998 | gb\|D19012 | 3.2e-48 | 10% | Mus musculus Mouse 3'-directed cDNA, MUSGS01209, clone mc0315 |
| OST3003 | gb\|U27502 | 1.3e-169 | 97% | Mus musculus Mus musculus lens major intrinsic protein (MIP) mRNA, complete cds |
| OST3004 | gb\|AA103385 | 1.9e-162 | 98% | Mus musculus mo23f02.r1 Life Tech mouse embryo 13 5dpc 10666014 Mus musculus cDNA clone 554427 5' similar to gb:Z15030_rna1 MYOSIN REGULATORY LIGHT CHAIN 2, VENTRICULAR (HUMAN); gb:X65979 M. musculus PLRLC-A mRNA for myosin light chain 2 (MOUSE) |
| OST3011 | gb\|AA035805 | 1.2e-98 | 99% | Mus musculus ml53a10.r1 Soares mouse embryo NbME13.5 14.5 Mus musculus cDNA clone 467226 5' similar to PIR:S28237 S28237 NADH dehydrogenase |
| OST3017 | gb\|AA050908 | 4.8e-123 | 92% | Mus musculus mj21e02.r1 Soares mouse embryo NbME13.5 14.5 Mus musculus cDNA clone 476762 5' similar to SW:AP17_RAT Q00380 CLATHRIN COAT ASSEMBLY PROTEIN AP17 |
| OST3018 | gb\|D83277 | 2.2e-235 | 99% | Mus musculus Mouse DNA for small GTP-binding protein S10, exon2 and complete cds |
| OST3032 | gb\|U49385 | 2.1e-76 | 99% | Mus musculus Mus musculus CTP synthetase homolog (CTPsH) mRNA, complete cds |
| OST3035 | gb\|L08651 | 1.8e-115 | 90% | Mus musculus Mus musculus large ribosomal subunit protein mRNA, complete cds |
| OST3037 | gb\|W90956 | 4.5e-34 | 74% | Mus musculus mf84h05.r1 Soares mouse embryo NbME13.5 14.5 Mus musculus cDNA clone 421017 5' |

FIG. 8i

| | | | | |
|---|---|---|---|---|
| OST3305 | gb\|D88453 | 1.0e-106 | 87% | Mus musculus Mouse mRNA |
| OST3312 | gb\|U78109 | 9.7e-59 | 66% | Mus musculus Mus musculus prepro-neurturin mRNA, complete cds |
| OST3323 | gb\|D43643 | 1.2e-132 | 91% | Mus musculus Mouse YL-1 mRNA for YL-1 protein (nuclear protein with DNA-binding ability), complete cds |
| OST3324 | gb\|X61399 | 2.2e-51 | 87% | Mus musculus Mouse F52 mRNA for a novel protein |
| OST3325 | gb\|D28476 | 6.5e-103 | 94% | Homo sapiens Human mRNA for KIAA0045 gene, complete cds |
| OST3349 | gb\|M18210 | 2.2e-52 | 94% | Mus musculus Mouse transcription factor S-II, clone PSII-3 |
| OST3352 | gb\|AA099569 | 4.9e-63 | 77% | Homo sapiens zk86b04.s1 Soares pregnant uterus NbHPU Homo sapiens cDNA clone 489679 3' |
| OST3354 | gb\|W53638 | 9.1e-69 | 92% | Mus musculus md14d10.r1 Soares mouse embryo NbME13.5 14.5 Mus musculus cDNA clone 368371 5' similar to SW:RNG3_HUMAN P25440 RING3 PROTEIN. [1] |
| OST3355 | gb\|U49185 | 4.1e-40 | 82% | Mus musculus Mus musculus occludin mRNA, complete cds |
| OST3366 | gb\|AA122835 | 2.1e-85 | 69% | Mus musculus mn24g03.r1 Beddington mouse embryonic region Mus musculus cDNA clone 538900 5' similar to gb:D00682 COFILIN (HUMAN); gb:D00472 Mouse mRNA for cofilin, complete cds and flanks (MOUSE) |
| OST3370 | gb\|S67058 | 4.6e-106 | 94% | Mus sp. Hoxa-4/Hox-1.4=Hoxa-4 [mice, Genomic, 2556 nt] |
| OST3371 | gb\|W31107 | 1.5e-50 | 71% | Homo sapiens zb85e12.r1 Soares senescent fibroblasts NbHSF Homo sapiens cDNA clone 310414 5' |
| OST3372 | gb\|W64859 | 2.2e-134 | 99% | Mus musculus me06f10.r1 Soares mouse embryo NbME13.5 14.5 Mus musculus cDNA clone 386731 5' similar to PIR:A55012 A55012 signal peptidase 25k chain - dog |
| OST3375 | gb\|AA015237 | 4.0e-44 | 10% | Mus musculus mh30a10.r1 Soares mouse placenta 4NbMP13.5 14.5 Mus musculus cDNA clone 443994 5' |
| OST3376 | gb\|M27347 | 4.2e-103 | 99% | Mus musculus Mus musculus p6-5 gene, 3' end |
| OST3388 | gb\|D50264 | 1.9e-117 | 98% | Mus musculus Mouse mRNA for phosphatidylinositol glycan class F, complete cds |
| OST3390 | gb\|W34022 | 3.6e-46 | 78% | Mus musculus mb01d09.r1 Soares mouse p3NMF19.5 Mus musculus cDNA clone 318929 5' |
| OST3393 | gb\|U60330 | 1.7e-208 | 93% | Mus musculus Mus musculus Ki antigen mRNA, complete cds |
| OST3404 | gb\|AA168895 | 6.3e-109 | 98% | Mus musculus ms41g02.r1 Life Tech mouse embryo 13 5dpc 10666014 Mus musculus cDNA clone 614162 5' similar to gb:M23419 INITIATION FACTOR 5A |
| OST3413 | gb\|N91837 | 3.3e-39 | 91% | Homo sapiens zb45f03.s1 Soares fetal lung NbHL19W Homo sapiens cDNA clone 306557 3' |
| OST3425 | gb\|W71116 | 1.3e-105 | 88% | Mus musculus me31d05.r1 Soares mouse embryo NbME13.5 14.5 Mus musculus cDNA clone 389097 5' |
| OST3428 | gb\|AA189339 | 3.4e-37 | 88% | Mus musculus mt79g04.r1 Soares mouse lymph node NbMLN Mus musculus cDNA clone 636150 5' |
| OST3441 | gb\|S51858 | 7.9e-66 | 77% | Mus sp. MO25 gene [mice, embryos, mRNA, 2322 nt] |
| OST3450 | gb\|X58426 | 7.1e-53 | 96% | Mus musculus Mouse mRNA for hepatic triglyceride lipase |
| OST3457 | gb\|W87064 | 9.0e-166 | 97% | Mus musculus mf58h05.r1 Soares mouse embryo NbME13.5 14.5 Mus musculus cDNA clone 418521 5' |
| OST3460 | gb\|AA185213 | 4.2e-134 | 99% | Mus musculus mu51g08.r1 Soares mouse lymph node NbMLN Mus musculus cDNA clone 642974 5' similar to TR:E243948 E243948 CHROMOSOME VII READING FRAME ORF YGL054C. |
| OST3480 | gb\|AA118567 | 9.4e-100 | 89% | Mus musculus mn12a08.r1 Beddington mouse embryonic region Mus musculus cDNA clone 537686 5' |
| OST3481 | gb\|X56906 | 1.0e-121 | 95% | Mus musculus Mouse OP-1 mRNA for osteogenic protein 1 |

FIG. 8j

| | | | | |
|---|---|---|---|---|
| OST3483 | gb\|X79446 | 1.4e-114 | 92% | Mus musculus M. musculus Odf1 mRNA for outer dense fiber protein of sperm tails |
| OST3485 | gb\|D83824 | 1.4e-75 | 86% | Homo sapiens similar to T cell-specific MAL |
| OST3492 | gb\|W09518 | 4.7e-139 | 92% | Mus musculus ma08d09.r1 Soares mouse p3NMF19.5 Mus musculus cDNA clone 303953 5' |
| OST3494 | gb\|W61666 | 1.1e-138 | 99% | Mus musculus md82d01.r1 Soares mouse embryo NbME13.5 14.5 Mus musculus cDNA clone 374881 5' similar to SW:GBG5_BOVIN P30670 GUANINE NUCLEOTIDE-BINDING PROTEIN G(I)/G(S)/G(O) GAMMA-5 SUBUNIT. [1] |
| OST3500 | gb\|U62483 | 2.1e-180 | 98% | Mus musculus Mus musculus ubiquitin conjugating enzyme (ubc4) mRNA, complete cds |
| OST3501 | gb\|D59851 | 6.8e-54 | 90% | Homo sapiens Human fetal brain cDNA 5' - end GEN-070H03 |
| OST3505 | gb\|W40883 | 3.9e-173 | 99% | Mus musculus mc39d07.r1 Soares mouse p3NMF19.5 Mus musculus cDNA clone 350893 5' |
| OST3508 | gb\|M23458 | 2.0e-119 | 90% | Mus musculus Mus musculus endogenous retroviruslike B-26 (distantly related to MulV) LTR |
| OST3516 | gb\|L14441 | 5.4e-177 | 90% | Rattus norvegicus Rat phosphotidylethanolamine N-methyltransferase mRNA, complete cds |
| OST3517 | gb\|AA015044 | 5.5e-114 | 97% | Mus musculus mh23f10.r1 Soares mouse placenta 4NbMP13.5 14.5 Mus musculus cDNA clone 443371 5' |
| OST3518 | gb\|AA061165 | 6.3e-99 | 91% | Mus musculus mj31f05.r1 Soares mouse embryo NbME13.5 14.5 Mus musculus cDNA clone 477729 5' similar to TR:E222933 E222933 SUPEROXIDE DISMUTASE |
| OST3521 | gb\|H33756 | 3.7e-70 | 87% | Rattus sp. EST110066 Rattus sp. cDNA 3' end |
| OST3531 | gb\|U19893 | 6.7e-34 | 80% | Rattus norvegicus Rattus norvegicus alpha actinin mRNA, complete cds |
| OST3534 | gb\|U37150 | 5.7e-31 | 83% | Bos taurus Bos taurus peptide methionine sulfoxide reductase (msrA) mRNA, complete cds |
| OST3545 | gb\|M93148 | 4.0e-103 | 84% | Mus musculus Mouse homeobox protein (Hox-1.11) gene, complete cds |
| OST3556 | gb\|W08748 | 1.9e-129 | 97% | Mus musculus mb48f02.r1 Soares mouse p3NMF19.5 Mus musculus cDNA clone 332667 5' |
| OST3558 | gb\|L03386 | 7.9e-132 | 97% | Rattus norvegicus Rattus norvegicus (clone RAHB2-5/8) zinc finger protein mRNA, 3' end cds |
| OST3561 | gb\|W13785 | 5.1e-64 | 99% | Mus musculus ma94c11.r1 Soares mouse p3NMF19.5 Mus musculus cDNA clone 318356 5' similar to SW:RS27_RAT P24051 40S RIBOSOMAL PROTEIN S27. [1] |
| OST3567 | gb\|AA050004 | 2.8e-48 | 78% | Mus musculus mj39d07.r1 Soares mouse embryo NbME13.5 14.5 Mus musculus cDNA clone 478477 5' |
| OST3571 | gb\|W75236 | 2.4e-113 | 91% | Mus musculus me53a07.r1 Soares mouse embryo NbME13.5 14.5 Mus musculus cDNA clone 391188 5' |
| OST3575 | gb\|AA080212 | 6.0e-90 | 93% | Mus musculus mj99a06.r1 Soares mouse p3NMF19.5 Mus musculus cDNA clone 484210 5' similar to gb:X58079 S-100 PROTEIN, ALPHA CHAIN (HUMAN) |
| OST3579 | gb\|S74622 | 1.1e-39 | 76% | Gallus gallus PP1M M21 subunit=protein phosphatase 1M 21 kda regulatory subunit {chickens, gizzard smooth muscle, mRNA, 1598 nt} |
| OST3582 | gb\|X74350 | 1.5e-74 | 99% | Mus musculus M. musculus XPAC Xerderma Pigmentosum group A Correcting gene, exon 6 |
| OST3601 | gb\|U50078 | 4.6e-138 | 89% | Homo sapiens Human guanine nucleotide exchange factor p532 mRNA, complete cds |
| OST3602 | gb\|R15062 | 2.3e-107 | 90% | Homo sapiens yf86h05.r1 Homo sapiens cDNA clone 29483 5' |
| OST3604 | gb\|M22756 | 4.9e-119 | 84% | Rattus norvegicus Rat 24-kDa subunit of mitochondrial NADH dehydrogenase mRNA, 3' end |
| OST3608 | gb\|U34994 | 5.4e-101 | 85% | Homo sapiens Human DNA-dependent |

FIG. 8k

| | | | | |
|---|---|---|---|---|
| OST3609 | gb\|AA165901 | 2.4e-129 | 96% | protein kinase catalytic subunit (DNA-PKcs) mRNA, complete cd Mus musculus mt75e03.r1 Soares mouse lymph node NbMLN Mus musculus cDNA clone 635740 5' |
| OST3631 | gb\|AA028590 | 2.1e-152 | 97% | Mus musculus mi21c12.r1 Soares mouse embryo NbME13.5 14.5 Mus musculus cDNA clone 464182 5' similar to WP:R01H2.6 CE00805 UBC |
| OST3642 | gb\|R85211 | 1.4e-47 | 74% | Homo sapiens yo41d11.s1 Homo sapiens cDNA clone 180501 3' similar to SP:S19586 S19586 N-METHYL-D-ASPARTATE RECEPTOR GLUTAMATE-BINDING CHAIN- |
| OST3645 | gb\|M14951 | 1.3e-104 | 90% | Mus musculus Mouse insulin-like growth factor II (IGF-II) mRNA, complete cds |
| OST3647 | gb\|U14721 | 1.7e-36 | 76% | Mus musculus Mus musculus c-abl oncogene (c-abl) gene, exons 2 and 3, partial cds |
| OST3651 | gb\|AA023146 | 1.4e-109 | 91% | Mus musculus mh67b03.r1 Soares mouse placenta 4NbMP13.5 14.5 Mus musculus cDNA clone 455981 5' similar to SW:A4P_HUMAN Q04941 INTESTINAL MEMBRANE A4 PROTEIN. [1] |
| OST3652 | gb\|S60494 | 3.1e-31 | 94% | Mus sp. gamma-phosphorylase kinase (alternatively spliced) [mice, muscle, Balb/C, Genomic, 4204 nt, segment 4 of 4] |
| OST3662 | gb\|U37427 | 3.1e-204 | 96% | Rattus norvegicus Rattus norvegicus phospholipid hydroperoxide glutathione peroxidase mRNA, complete cds |
| OST3669 | gb\|W55918 | 3.0e-35 | 86% | Homo sapiens zc03f12.s1 Soares parathyroid tumor NbHPA Homo sapiens cDNA clone 321263 3' similar to WP:E04F6.2 CE01214 |
| OST3681 | gb\|W55833 | 7.6e-94 | 93% | Mus musculus md07b01.r1 Soares mouse embryo NbME13.5 14.5 Mus musculus cDNA clone 367657 5' similar to gb:D37874 Mouse FcRn gene. (MOUSE) |
| OST3694 | gb\|W38194 | 5.4e-71 | 93% | Homo sapiens zc15e05.s1 Soares parathyroid tumor NbHPA Homo sapiens cDNA clone 322400 3' |
| OST3700 | gb\|AA038243 | 4.9e-171 | 99% | Mus musculus mi82d08.r1 Soares mouse p3NMF19.5 Mus musculus cDNA clone 473103 5' similar to SW:SARL_RABIT P42532 SARCOLIPIN. [1] |
| OST3703 | gb\|W47847 | 7.8e-71 | 82% | Mus musculus mc82f12.r1 Soares mouse embryo NbME13.5 14.5 Mus musculus cDNA clone 355055 5' |
| OST3704 | gb\|AA048648 | 4.6e-68 | 99% | Mus musculus mj33a07.r1 Soares mouse embryo NbME13.5 14.5 Mus musculus cDNA clone 477876 5' |
| OST3708 | gb\|AA002275 | 7.4e-89 | 97% | Mus musculus mg43h01.r1 Soares mouse embryo NbME13.5 14.5 Mus musculus cDNA clone 426577 5' similar to gb:M73704 PHOSPHATIDYLINOSITOL (HUMAN) |
| OST3716 | gb\|AA034685 | 8.2e-119 | 90% | Mus musculus mi56h10.r1 Soares mouse embryo NbME13.5 14.5 Mus musculus cDNA clone 467587 5' similar to gb:L19527 60S RIBOSOMAL PROTEIN L27 |
| OST3729 | gb\|W19303 | 2.9e-97 | 85% | Homo sapiens zb25d02.r1 Soares fetal lung NbHL19W Homo sapiens cDNA clone 303075 5' |
| OST3731 | gb\|W11502 | 1.3e-131 | 93% | Mus musculus ma80h06.r1 Soares mouse p3NMF19.5 Mus musculus cDNA clone 317051 5' similar to SW:PRCF_HUMAN P40306 PROTEASOME COMPONENT MECL-1 PRECURSOR |
| OST3735 | gb\|AA014575 | 5.2e-100 | 97% | Mus musculus mi67g07.r1 Soares mouse embryo NbME13.5 14.5 Mus musculus cDNA clone 468636 5' similar to SW:SYRM_YEAST P38714 ARGINYL-TRNA SYNTHETASE, MITOCHONDRIAL PRECURSOR |
| OST3757 | gb\|W77924 | 2.6e-99 | 83% | Homo sapiens zd71f04.r1 Soares fetal heart NbHH19W Homo sapiens cDNA clone 346111 5' |
| OST3759 | gb\|X64840 | 7.6e-51 | 97% | Mus musculus M. musculus ALF1 mRNA |
| OST3767 | gb\|C18536 | 5.2e-39 | 69% | Homo sapiens Human placenta cDNA 5'-end GEN-563H06 |
| OST3775 | gb\|D18282 | 1.6e-57 | 97% | Mus musculus Mouse 3'-directed cDNA, MUSGS00768, clone md0842 |

FIG. 81

| | | | | |
|---|---|---|---|---|
| OST3788 | gb|AA014426 | 9.7e-55 | 10% | Mus musculus mg84b01.r1 Soares mouse embryo NbME13.5 14.5 Mus musculus cDNA clone 439657 5' similar to SW:NB7M_BOVIN Q02367 NADH-UBIQUINONE OXIDOREDUCTASE B17 SUBUNIT |
| OST3789 | gb|D13544 | 9.5e-67 | 97% | Mus musculus Mouse mRNA for primase small subunit, complete cds |
| OST3807 | gb|W26968 | 3.8e-51 | 80% | Homo sapiens 16h7 Human retina cDNA randomly primed sublibrary Homo sapiens cDNA |
| OST3818 | gb|M28248 | 3.8e-48 | 96% | unidentified cloning vector Moloney murine leukemia virus retroviral vector pLXSN, complete genome |
| OST3819 | gb|T55632 | 3.8e-35 | 81% | Homo sapiens yb39b03.r1 Homo sapiens cDNA clone 73517 5' similar to SP:T20G5.10 CE00629 |
| OST3827 | gb|AA046830 | 1.2e-67 | 84% | Homo sapiens zf12h11.s1 Soares fetal heart NbHH19W Homo sapiens cDNA clone 376773 3' |
| OST3831 | gb|W70777 | 3.5e-121 | 99% | Mus musculus mr44a02.r1 Soares mouse embryo NbME13.5 14.5 Mus musculus cDNA clone 390314 5' |
| OST3839 | gb|M86008 | 1.4e-103 | 86% | Homo sapiens EST02533 Homo sapiens cDNA clone HFBCY19 similar to Hypothetical 43.5K protein |
| OST3843 | gb|Z82190 | 2.8e-51 | 88% | Homo sapiens Human DNA sequence *** SEQUENCING IN PROGRESS *** from clone 180M12; HTGS phase 1 |
| OST3849 | gb|W64986 | 1.3e-173 | 94% | Mus musculus me04c05.r1 Soares mouse embryo NbME13.5 14.5 Mus musculus cDNA clone 386504 5' similar to SW:VSH7_DICDI P14327 VEGETATIVE SPECIFIC PROTEIN H7. [1] |
| OST3851 | gb|U51037 | 1.0e-135 | 84% | Mus musculus Mus musculus 11-zinc-finger transcription factor (CTCF) mRNA, complete cds |
| OST3858 | gb|X56135 | 4.7e-237 | 97% | Mus musculus Mouse mRNA for prothymosin alpha |
| OST3864 | gb|D19493 | 9.8e-33 | 95% | Mus musculus Mouse 3'-directed cDNA, MUSGS00881, clone mb0610 |
| OST3869 | gb|W41525 | 4.4e-100 | 85% | Mus musculus mc45b04.r1 Soares mouse p3NMF19.5 Mus musculus cDNA clone 351439 5' |
| OST3897 | gb|W10485 | 3.8e-97 | 95% | Mus musculus ma53e06.r1 Soares mouse p3NMF19.5 Mus musculus cDNA clone 314434 5' |
| OST3903 | gb|W59388 | 1.2e-108 | 86% | Mus musculus md79f02.r1 Soares mouse embryo NbME13.5 14.5 Mus musculus cDNA clone 374619 5' similar to gb:U07151 ADB-RIBOSYLATION FACTOR-LIKE PROTEIN 3 (HUMAN) |
| OST3905 | gb|D85430 | 8.0e-102 | 92% | Mus musculus Mouse Murr1 mRNA, exon |
| OST3909 | gb|AA020459 | 1.2e-80 | 94% | Mus musculus mh61a06.r1 Soares mouse placenta 4NbMP13.5 14.5 Mus musculus cDNA clone 455410 5' |
| OST3917 | gb|Z44044 | 8.7e-81 | 87% | Homo sapiens H. sapiens partial cDNA sequence; clone c-lrc07 |
| OST3924 | gb|J04699 | 3.9e-32 | 84% | Mus musculus Mouse nicotinic acetylcholine receptor beta subunit (nAChRE) gene, complete cds |
| OST3925 | gb|W23511 | 1.2e-88 | 76% | Homo sapiens zb46e02.r1 Soares fetal lung NbHL19W Homo sapiens cDNA clone 306650 5' |
| OST3931 | gb|U14957 | 1.6e-36 | 81% | Homo sapiens Human 53K isoform of Type II phosphatidylinositol-4-phosphate 5-kinase (PIPK) mRNA, complete cds |
| OST3945 | gb|W15004 | 1.6e-122 | 97% | Mus musculus mb25c09.r1 Soares mouse p3NMF19.5 Mus musculus cDNA clone 330448 5' |
| OST3957 | gb|AA051293 | 2.8e-143 | 96% | Mus musculus mj40h10.r1 Soares mouse embryo NbME13.5 14.5 Mus musculus cDNA clone 478627 5' similar to SW:TGFB_HUMAN P22064 TRANSFORMING GROWTH FACTOR BETA-1 BINDING PROTEIN PRECURSOR |
| OST3960 | gb|D38614 | 1.1e-88 | 82% | Mus musculus Mouse 921-S mRNA for presynaptic protein, complete cds |
| OST3961 | gb|U67988 | 6.6e-37 | 77% | Homo sapiens Human guanylate kinase associated protein (GKAP) mRNA, complete cds |

FIG. 8m

| | | | | |
|---|---|---|---|---|
| OST3971 | gbIW45926 | 9.6e-55 | 94% | Mus musculus mc79e04.r1 Soares mouse embryo NbME13.5 14.5 Mus musculus cDNA clone 354750 5' |
| OST3988 | gbIM13524 | 2.6e-111 | 90% | Mus musculus Mouse serum amyloid A pseudogene (psi-SAA) |
| OST3993 | gbIR16778 | 4.7e-45 | 82% | Homo sapiens yf33a08.s1 Homo sapiens cDNA clone 128630 3' |
| OST4002 | gbIAA000314 | 1.9e-112 | 96% | Mus musculus mg34e07.r1 Soares mouse embryo NbME13.5 14.5 Mus musculus cDNA clone 425700 5' |
| OST4003 | gbIL37297 | 2.9e-121 | 91% | Mus musculus Mus musculus (clone B6) myeloid secondary granule protein mRNA |
| OST4011 | gbIL26664 | 2.0e-155 | 94% | Mus musculus Mus musculus expressed sequence tag EST F032 |
| OST4028 | gbID87470 | 7.5e-93 | 92% | Homo sapiens Human mRNA for KIAA0280 gene, partial cds |
| OST4033 | gbIAA084704 | 2.2e-54 | 88% | Homo sapiens zn05f04.s1 Stratagene hNT neuron (#937233) Homo sapiens cDNA clone 546559 3' similar to TR:G600529 G600529 NADH UBIQUINONE OXIDOREDUCTASE SUBUNIT |
| OST4051 | gbIF03500 | 7.6e-63 | 86% | Homo sapiens H. sapiens partial cDNA sequence; clone c-lzd08 |
| OST4061 | gbIW30618 | 3.1e-118 | 97% | Mus musculus mc10h12.r1 Soares mouse p3NMF19.5 Mus musculus cDNA clone 348167 5' |
| OST4070 | gbIW36515 | 6.0e-135 | 94% | Mus musculus mb76g12.r1 Soares mouse p3NMF19.5 Mus musculus cDNA clone 335398 5' |
| OST4073 | gbIX82021 | 2.0e-105 | 91% | Rattus norvegicus R. norvegicus mRNA for heat shock related protein |
| OST4074 | gbID63704 | 3.3e-140 | 86% | Rattus norvegicus Rat mRNA for dihydropyrimidinase, complete cds |
| OST4106 | gbIW75804 | 1.1e-84 | 93% | Mus musculus me67a06.r1 Soares mouse embryo NbME13.5 14.5 Mus musculus cDNA clone 400594 5' |
| OST4114 | gbIW20730 | 6.5e-90 | 96% | Mus musculus mb96g01.r1 Soares mouse p3NMF19.5 Mus musculus cDNA clone 337296 5' |
| OST4131 | gbIAA044274 | 2.4e-33 | 69% | Homo sapiens zk54h03.s1 Soares pregnant uterus NbHPU Homo sapiens cDNA clone 486677 3' |
| OST4134 | gbIH31489 | 3.0e-84 | 85% | Rattus sp. EST105564 Rattus sp. cDNA 3' end |
| OST4140 | gbIW71052 | 3.7e-121 | 91% | Mus musculus me27f01.r1 Soares mouse embryo NbME13.5 14.5 Mus musculus cDNA clone 388729 5' similar to SW:YBHB_YEAST P38182 HYPOTHETICAL 13.6 KD PROTEIN IN PET112-ILS1 INTERGENIC REGION. [1] |
| OST4142 | gbIC07091 | 5.7e-74 | 89% | Rattus norvegicus similar to none |
| OST4144 | gbIX56135 | 4.4e-41 | 83% | Mus musculus Mouse mRNA for prothymosin alpha |
| OST4148 | gbIW54510 | 1.5e-135 | 91% | Mus musculus md08h09.r1 Soares mouse embryo NbME13.5 14.5 Mus musculus cDNA clone 367841 5' similar to PIR:A56059 A56059 protein-tyrosine-phosphatase |
| OST4149 | gbIU36393 | 2.6e-111 | 96% | Mus musculus Mus musculus transcription factor TFEB mRNA, partial cds |
| OST4154 | gbIX56046 | 1.3e-161 | 96% | Mus musculus Mouse mRNA (clone lambda-16) for hypothetical protein A |
| OST4155 | gbIX05900 | 3.5e-58 | 85% | Rattus norvegicus Rat mRNA for lens betaB1-crystallin (pRLbeta B1-3) |
| OST4166 | gbIU53859 | 8.0e-169 | 90% | Rattus norvegicus Rattus norvegicus calpain small subunit (css1) mRNA, partial cds |
| OST4174 | gbIU41395 | 1.3e-38 | 84% | Mus musculus Mus musculus X inactive specific transcript (Xist) gene, cosmid MB4-14A, fragment 2 |
| OST4191 | gbIX63507 | 2.0e-75 | 81% | Mus musculus M. musculus HOX-3.5 gene |
| OST4192 | gbIW85357 | 2.2e-83 | 82% | Mus musculus mf49h12.r1 Soares mouse embryo NbME13.5 14.5 Mus musculus cDNA clone 408455 5' similar to SW:GLYM_HUMAN p34897 SERINE HYDROXYMETHYLTRANSFERASE MITOCHONDRIAL |
| OST4194 | gbIW34635 | 8.9e-38 | 87% | Mus musculus mc31e07.r1 Soares mouse p3NMF19.5 Mus musculus cDNA clone 350148 5' |

FIG. 8n

| | | | | |
|---|---|---|---|---|
| OST4196 | gb\|W41301 | 3.1e-39 | 99% | Mus musculus mc43h06.r1 Soares mouse p3NMF19.5 Mus musculus cDNA clone 351323 5' |
| OST4223 | gb\|AA203787 | 2.7e-89 | 90% | Mus musculus mu60f12.r1 Soares mouse lymph node NbMLN Mus musculus cDNA clone 643823 5' |
| OST4228 | gb\|S51016 | 9.3e-205 | 92% | Bos taurus E2 (25K) =multiubiquitinating enzyme [cattle, thymus, mRNA, 825 nt] |
| OST4229 | gb\|Z31263 | 4.9e-70 | 97% | Mus musculus M. musculus expressed sequence tag MTEST7 |
| OST4235 | gb\|W53187 | 3.0e-173 | 97% | Mus musculus md19a07.r1 Soares mouse embryo NbME13.5 14.5 Mus musculus cDNA clone 368820 5' similar to WP: C32D5.9 CE01849 |
| OST4243 | gb\|AA048921 | 2.3e-4.0 | 86% | Mus musculus mj47e11.r1 Soares mouse embryo NbME13.5 14.5 Mus musculus cDNA clone 479276 5' similar to gb:U13705 Mus musculus domesticus C57BL/6J plasma glutathione (MOUSE) |
| OST4245 | gb\|H10216 | 9.9e-80 | 75% | Homo sapiens ym02f05.s1 Homo sapiens cDNA clone 46710 3' |
| OST4247 | gb\|AA023146 | 1.5e-115 | 96% | Mus musculus mh67b03.r1 Soares mouse placenta 4NbMP13.5 14.5 Mus musculus cDNA clone 455981 5' similar to SW:A4P_HUMAN Q04941 INTESTINAL MEMBRANE A4 PROTEIN. [1] |
| OST4251 | gb\|AA070774 | 8.7e-154 | 98% | Homo sapiens zm53g11.s1 Stratagene fibroblast (#937212) Homo sapiens cDNA clone 529412 3' |
| OST4254 | gb\|W54737 | 2.4e-82 | 10% | Mus musculus md10a04.r1 Soares mouse embryo NbME13.5 14.5 Mus musculus cDNA clone 367950 5' |
| OST4258 | gb\|AA013789 | 4.3e-169 | 90% | Mus musculus mh13d03.r1 Soares mouse placenta 4NbMP13.5 14.5 Mus musculus cDNA clone 442373 5' similar to PIR:JC2472 JC2472 RE protein - human |
| OST4281 | gb\|U16175 | 4.0e-40 | 63% | Mus musculus Mus musculus thrombospondin 3 (Thbs3) gene, partial cds and mucin 1 (Muc1) gene, complete cds |
| OST4283 | gb\|AA007519 | 8.9e-52 | 81% | Homo sapiens zh98e12.r1 Soares fetal liver spleen 1NFLS S1 Homo sapiens cDNA clone 429358 5' |
| OST4288 | gb\|AA000024 | 1.4e-135 | 96% | Mus musculus mg33e06.r1 Soares mouse embryo NbME13.5 14.5 Mus musculus cDNA clone 425602 5' similar to gb:X03920_rna2 M. musculus GSHPx gene (MOUSE) |
| OST4315 | gb\|M18210 | 6.4e-62 | 96% | Mus musculus Mouse transcription factor S-II, clone PSII-3 |
| OST4319 | gb\|J04696 | 2.0e-127 | 95% | Mus musculus Mouse glutathions S-transferase class mu (GST5-5) mRNA, complete cds |

FIG. 8o

INDEXED LIBRARY OF CELLS CONTAINING GENOMIC MODIFICATIONS AND METHODS OF MAKING AND UTILIZING THE SAME

The present application is a divisional of U.S. application Ser. No. 08/942,806, filed October 2, 1997 now U.S. Pat. No. 6,207,371 which is a continuation-in-part of U.S. application Ser. No. 08/726,867, filed Oct. 4, 1996 now U.S. Pat. No. 6,186,566, and Ser. No. 08/728,963, filed Oct. 11, 1996 now ABN. The application also claims priority to U.S. application Ser. No. 08/907,598, filed Aug. 8, 1997. The disclosures of the above applications are herein incorporated by reference.

1.0. FIELD OF THE INVENTION

The invention relates to an indexed library of genetically altered cells and methods of organizing the cells into an easily manipulated and characterized Library. The invention also relates to methods of making the library, vectors for making insertion mutations in genes, methods of gathering sequence information from each member clone of the Library, and methods of isolating a particular clone of interest from the Library.

2.0. BACKGROUND OF THE INVENTION

The general technologies of targeting mutations into the genome of cells, and the process of generating mouse lines ii; from genetically altered embryonic stem (ES) cells with specific genetic lesions are well known (Bradley, 1991, Cur. Opin. Biotech. 2:823–829). A random method of generating genetic lesions in cells (called gene, or promoter, trapping) has been developed in parallel with the targeted methods of genetic mutation (Allen et al., 1988 Nature 333(6176):852–855; Brenner et al., 1989, Proc. Natl. Acad. Sci. U.S.A. 86(14):5517–5521; Chang et al., 1993, Virology 193(2):737–747; Friedrich and Soriano, 1993, Insertional mutagenesis by retroviruses and promoter traps in embryonic stem cells, p. 681–701. In Methods Enzymol., vol. 225., P. M. Wassarman and M. L. DePamphilis (ed.), Academic Press, Inc., San Diego; Friedrich and Soriano, 1991, Genes Dev. 5(9):1513–1523; Gossler et al., 1989, Science 244 (4903):463–465; Kerr et al., 1989, Cold Spring Harb. Symp. Quant. Biol. 2:767–776; Reddy et al., 1991, J. Virol. 65(3):1507–1515; Reddy et al., 1992, Proc. Natl. Acad. Sci. U.S.A. 89(15):6721–6725; Skarnes et al., 1992, Genes Dev. 6(6):903–918; von Melchner and Ruley, 1989, J. Virol. 63(8):3227–3233; Yoshida et al., 1995, Transgen. Res. 4:277–287). Gene trapping provides a means to create a collection of random mutations by inserting fragments of DNA into transcribed genes. Insertions into transcribed genes are selected over the background of total insertions since the mutagenic DNA encodes an antibiotic resistance gene or some other selectable marker. The selectable marker lacks its own promoter and enhancer and must be expressed by the endogenous sequences that flank the marker after it has integrated. Using this approach, transcription of the selectable marker is activated and the cell gene is concurrently mutated. This type of strict selection makes it possible to easily isolate thousands of ES cell colonies, each with a unique mutagenic insertion.

Collecting mutants on a large-scale has been a powerful genetic technique commonly used for organisms which are more amenable to such analysis than mammals. These organisms, such as *Drosophila melanogastor*, yeast *Saccharomyces cerevisiae*, and plants such as *Arabadopsis thalia* are small, have short generation times and small genomes (Bellen et al., 1989, Genes Dev. 3(9):1288–1300; Bier et al., 1989, Genes Dev. 3(9):1273–1287; Hope, 1991, Develop. 113(2):399–408. These features allow an investigator to rear many thousands or millions of different mutant strains without requiring unmanageable resources. However, these type of organisms have only limited value in the study of biology relevant to human physiology and health. It is therefore important to have the power of large-scale genetic analysis available for the study of a mammalian species that can aid in the study of human disease. Given that the entire human genome is presently being sequenced, the comprehensive genetic analysis of a related mammalian species will provide a means to determine the function of genes cloned from the human genome. At present, rodents, and particularly mice, provide the best model for genetic manipulation and analysis of mammalian physiology.

Gene trapping has been used as an analytical tool to identify genes and regulatory regions in a variety of animal cell types. One system that has proved particularly useful is based on the use of ROSA (reverse orientation splice acceptor) retroviral vectors (Friedrich and Soriano, 1991 and 1993).

The ROSA system can generate mutations that result in a detectable homozygous phenotype with a high frequency. About 50% of all the insertions caused embryonic lethality. The specifically mutated genes may easily be cloned since the gene trapping event produces a fusion transcript. This fusion transcript has trapped exon sequences appended to the sequences of the selectable marker allowing the latter to be used as a tag in polymerase chain reaction (PCR)-based protocols, or by simple cDNA cloning. Examples of genes isolated by these methods include a transcription factor related to human TEF-1 (transcription enhancer factor-1) which is required in the development of the heart (Chen et al., 1994, Genes Devel. 8:2293–2301. Another (spock), is distantly related to yeast genes encoding secretion proteins and is important during gastrulation.

The above experiments have established that the ROSA system is an effective analytical tool for genetic analysis in mammals. However, the structure of many ROSA vectors selects for the "trapping" of 5' exons which, in many cases, do not encode proteins. Such a result is adequate where one wishes to identify and eventually clone control (i.e., promoter or enhancer) sequences, but is not optimal where the generation of insertion-inactivated null mutations is desired, and relevant coding sequence is needed. Thus, the construction of large-scale mutant (preferably null mutant) libraries requires the use of vectors that have been designed to select for insertion events that have occurred within the coding region of the mutated genes as well as vectors that are not limited to detecting insertions into expressed genes.

3.0. SUMMARY OF THE INVENTION

An object of the present invention is to provide a set of genetically altered cells (the 'Library'). The genetic alterations are of sufficient randomness and frequency such that the combined population of cells in the Library represent mutations in essentially every gene found in the cell's genome. The Library is used as a source for obtaining specifically mutated cells, cell lines derived from the individually mutated cells, and cells for use in the production of transgenic non-human animals.

A further object is to provide the vectors, both DNA and retroviral based, that may be used to generate the Library. Typically, at least two distinct vector designs will be used in order to mutate genes that are actively expressed in the target cell, and genes that are not expressed in the target cell. Combining the mutant cells obtained using both types of vectors best ensures that the Library provides a comprehensive set of gene mutations.

A particularly useful vector class contemplated by the present invention includes a vector for inserting foreign exons into animal cell transcripts that comprises a selectable marker, a promoter element operatively positioned 5' to the selectable marker, a splice donor site operatively positioned 3' to the selectable marker, and a second mutagenic foreign polynucleotide sequence located upstream from the promoter element that disrupts, or otherwise "poisons", the splicing or read-through expression of the endogenous cellular transcript. Typically, the mutagenic foreign polynucleotide sequence may incorporate a polyadenylation (pA) site, a nested set of stop codons in each of the three reading frames, splice acceptor and splice donor sequences in operable combination, a mutagenic exon, or any mixture of mutagenic features that effectively prevent the expression of the cellular gene. For example, a polyadenylation sequence may be incorporated in addition to or in lieu of the splice donor sequence. A preferred organization for the mutagenic polynucleotide sequence comprises a polyadenylation site positioned upstream from a selectable marker which is in turn located upstream from a splice acceptor sequence. Preferably, such a vector does not comprise a transcription terminator or polyadenylation site operatively positioned relative to the coding region of the selectable marker, and shall not comprise a splice acceptor site operatively positioned between the promoter element and the initiation codon of said selectable marker.

An additional vector contemplated by the present invention is designed to replace the normal 31 end of an animal cell transcript with a foreign exon. Such a vector shall generally be engineered to comprise a selectable marker, a splice acceptor site operatively positioned upstream (5') from the initiation codon of the selectable marker, and a polyadenylation site operatively positioned downstream (3') from the termination codon (3' end) of the selectable marker. Preferably, the vector will not comprise a promoter element operatively positioned upstream from the coding region of the selectable marker, and will not comprise a splice donor sequence operatively positioned between the 3' end of the coding region of the selectable marker and the polyadenylation site.

Yet another vector contemplated by the present invention is a vector designed to insert a mutagenic foreign polynucleotide sequence within an animal cell transcript (i.e., the foreign polynucleotide sequence is flanked on both sides by endogenous exons). As described above, the mutagenic foreign polynucleotide sequence may be any sequence that disrupts the normal expression of the gene into which the vector has integrated. Optionally, the vector may additionally incorporate a selectable marker, a splice acceptor site operatively positioned 5' to the initiation codon of the selectable marker, a splice donor site operatively positioned 3' to said selectable marker. Preferably, this vector shall not comprise a polyadenylation site operatively positioned 3' to the coding region of said selectable marker, and shall not comprise a promoter element operatively positioned 5' to the coding region of said selectable marker.

An additional embodiment of the present invention is a library of genetically altered cells that have been treated to stably incorporate one or more types of the vectors described above. The presently described library of cultured animal cells may be made by a process comprising the steps of treating (i.e., infecting, transfecting, retrotransposing, or virtually any other method of introducing polynucleotides into a cell) a population of cells to stably integrate a vector that mediates the splicing of a foreign exon internal to a cellular transcript, transfecting another population of cells to stably integrate a vector that mediates the splicing of a foreign exon 5' to an exon of a cellular transcript, and selecting for transduced cells that express the products encoded by the foreign exons.

Alternatively, an additional embodiment of the present invention describes a mammalian cell library made by a method comprising the steps of: transfecting a population of cells with a vector capable of expressing a selectable marker in the cell only after the vector inserts into the host genome; transfecting or infecting a population of cells with a vector containing a selectable marker that is substantially only expressed by cellular control sequences (after the vector integrates into the host cells genome); and growing the transfected cells under conditions that select for the expression of the selectable marker.

In an additional embodiment of the present invention, the two populations of transfected cells will be individually grown under selective conditions, and the resulting mutated population of cells collectively comprises a substantially comprehensive library of mutated cells.

In an additional embodiment of the present invention, the individual mutant cells in the library are separated and clonally expanded. Additionally, the clonally expanded mutant cells may then be analyzed to ascertain the DNA sequence, or partial DNA sequence of the mutated host gene.

The presently described methods of making, organizing, and indexing libraries of mutated animal cells are also broadly applicable to virtually any eukaryotic cells that may be genetically manipulated and grown in culture.

The invention provides for sequencing every gene mutated in the Library. The resulting sequence database subsequently serves as an index for the library. In essence, every cell line in the Library is individually catalogued using the partial sequence information. The resulting sequence is specific for the mutated gene since the present methods are designed to obtain sequence information from exons that have been spliced to the marker sequence. Since the coverage of the mutagenesis is preferably the entire set of genes in the genome, the resulting Library sequence database contains sequence from essentially every gene in the cell. From this database, a gene of interest can be identified. Once identified, the corresponding mutant cell may be withdrawn from the Library based on cross reference to the sequence data.

An additional embodiment of the invention provides for methods of isolating mutations of interest from the Library. Two methods are proposed for obtaining individual mutant cell lines from the Library. The first provides a scheme where clones of the cells generated using the above vectors are pooled into sets of defined size. Using the procedure described below which utilizes reverse transcription (RT) and polymerase chain reaction (PCR), a cell line with a mutation in a gene whose sequence is partly or wholly known is isolated from organized sets of these pools. A few rounds of this screening procedure results in the isolation of the desired individual cell line.

A second procedure involves the sequencing of regions flanking the vector insertion sites in the various cells in the library. The sequence database generated from these data effectively constitutes an index of the clones in the library that may be used to identify cells having mutations in specific genes.

4.0. DESCRIPTION OF THE FIGURES

FIG. 1. Shows a diagrammatic representation of 5 different vectors that are generally representative of the type of vectors that may be used in the present invention.

Figure 2:
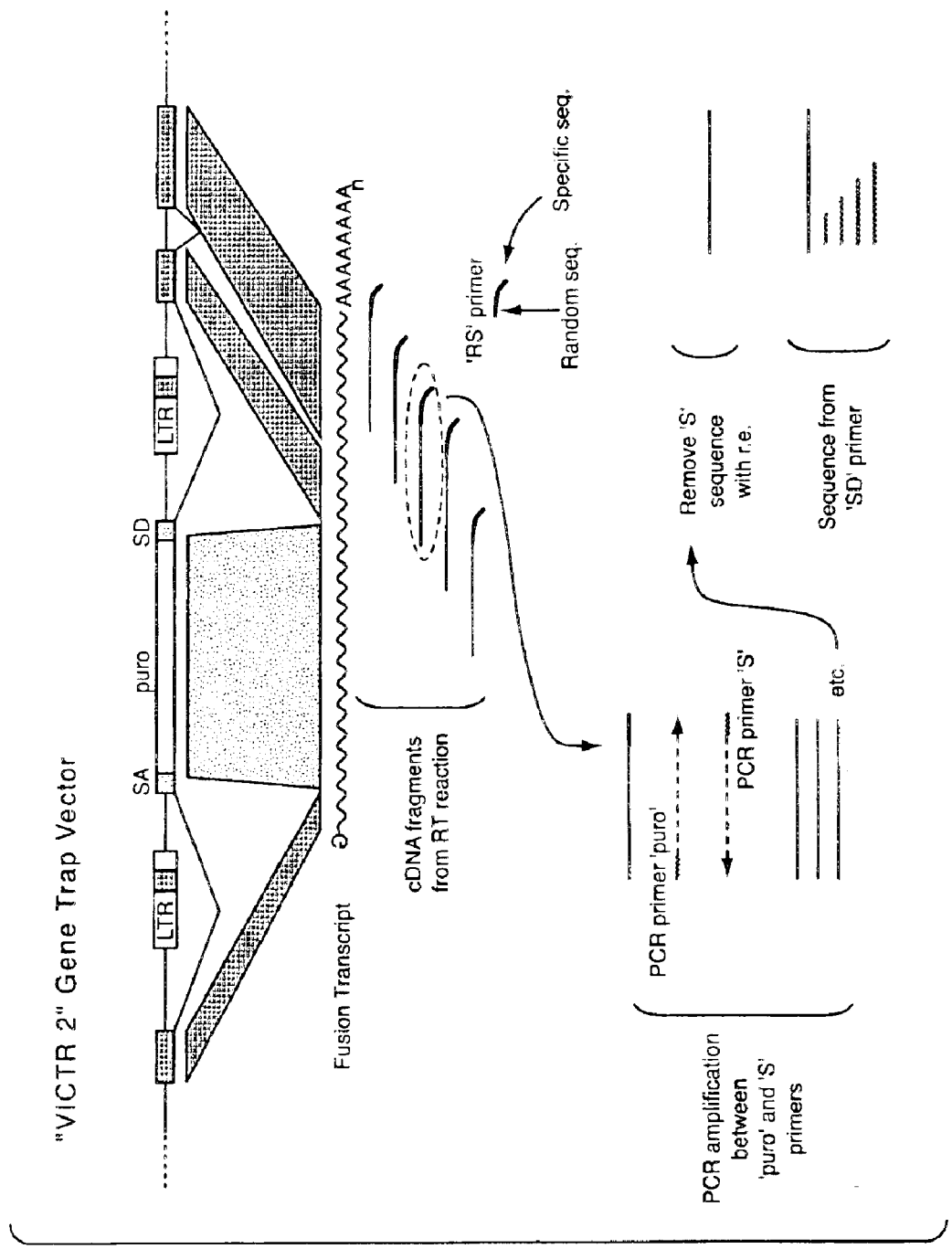

FIG. 2. Shows a general strategy for identifying "trapped" cellular sequences by PCR analysis of the cellular exons that flank the foreign intron introduced by the VICTR 2 vector.

Figure 3:
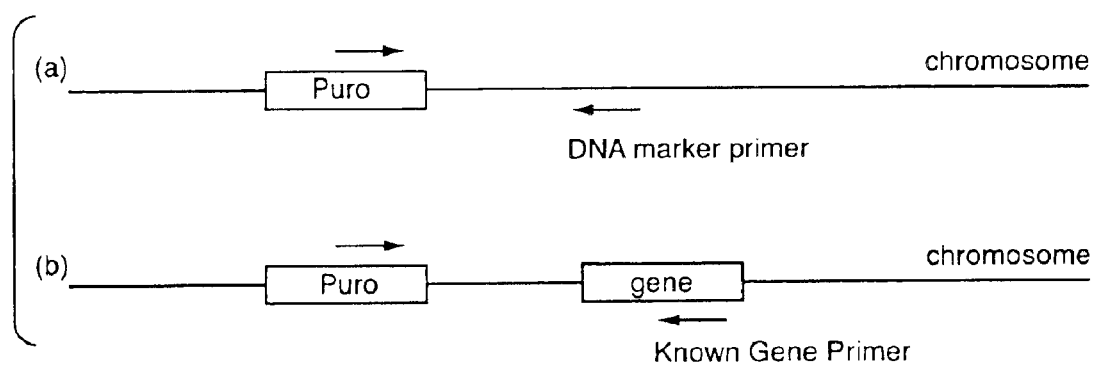

FIG. 3 shows a PCR based strategy for identifying tagged genes by chromosomal location.

Figure 4:
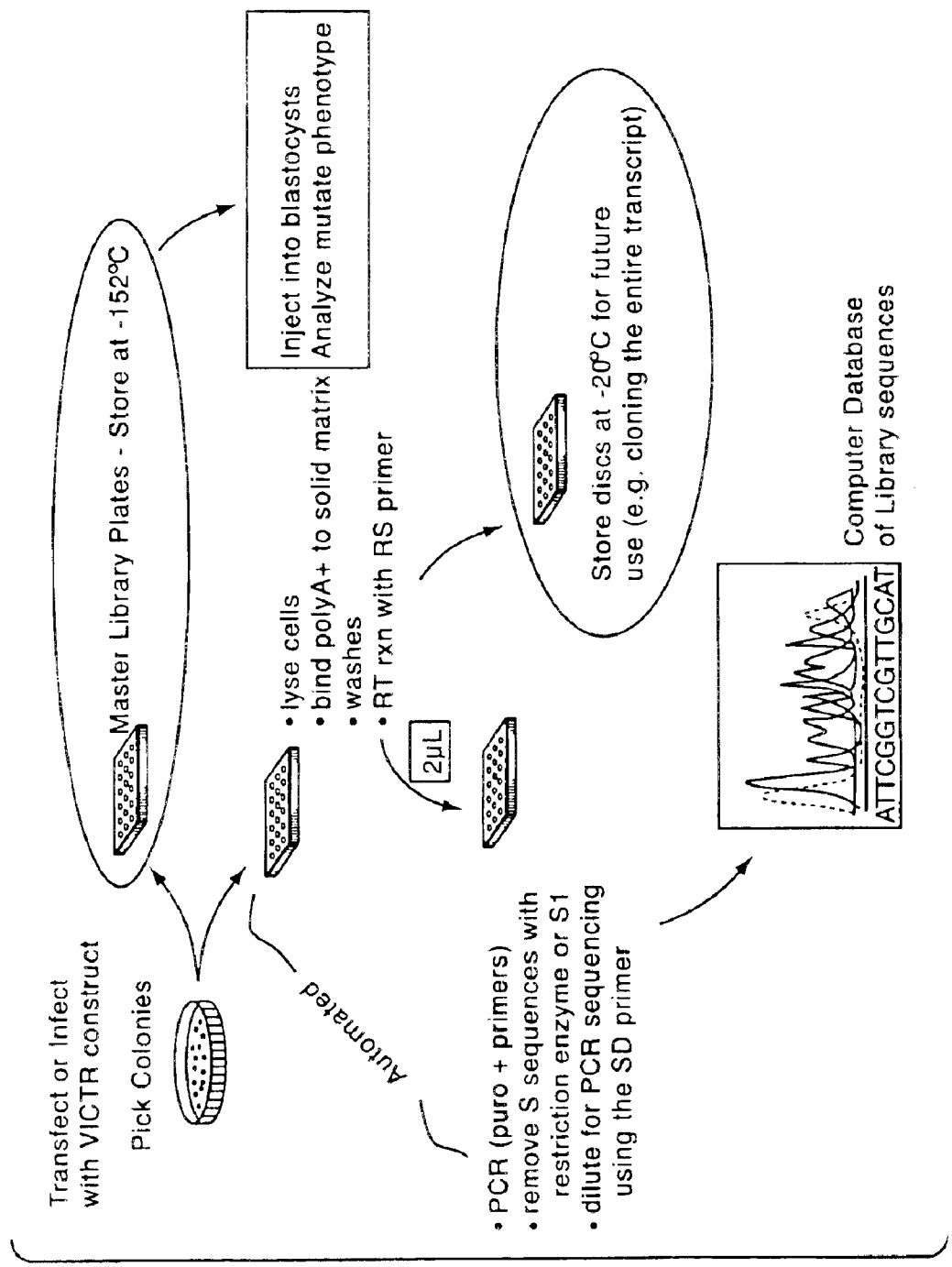

FIG. 4. Is a diagrammatic representation of a strategy of identifying or indexing the specific clones in the library via PCR analysis and sequencing of mRNA samples obtained from the cells in the library.

FIG. 5. Is a diagrammatic representation of a method of isolating positive clones by screening pooled mutant cell clones.

FIG. 6. Partial nucleic acid or predicted amino acid sequence data from 9 clones (OST1-9) isolated using the described techniques aligned with similar sequences from previously characterized genes.

Figure 7:
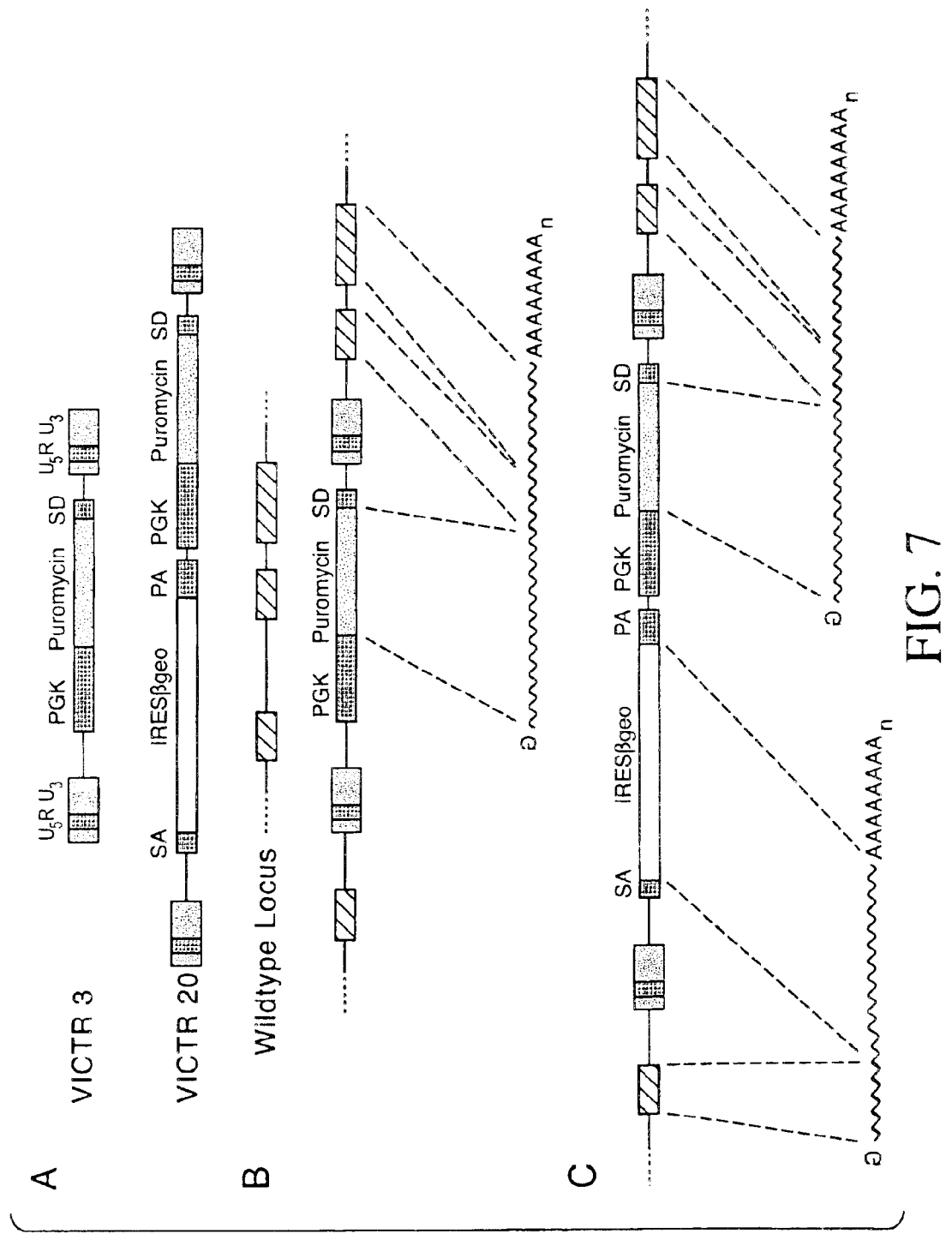

FIGS. 7A–C. Provide a diagrammatic representation of VICTRs 3 and 20 as well as the transcripts that result after integration into a hypothetical region of the target cell genome (i.e., "Wildtype" Locus).

FIGS. 8a–o. Provide a representative list of a portion of the known genes that have been identified using the disclosed methods and technology.

5.0. DETAILED DESCRIPTION OF THE INVENTION

The present invention describes a novel indexed library containing a substantially comprehensive set of mutations in the host cell genome, and methods of making and using the same. The presently described Library comprises as a set of cell clones that each possess at least one mutation (and preferably a single mutation) caused by the insertion of DNA that is foreign to the cell. For the purposes of the present invention, "foreign" polynucleotide sequences can be any sequences that are newly introduced to a cell, do not naturally occur in the cell at the engineered region of the chromosome, or occur in the cell but are not organized to provide an identical function to that provided in the engineered vector.

The particularly novel features of the Library include the methods of construction, and indexing. To index the library, the mutant cells of the library are clonally expanded and each mutated gene is at least partially sequenced. The Library thus provides a novel tool for assessing the specific function of a given gene. The insertions cause a mutation which allow for essentially every gene represented in the Library to be studied using genetic techniques either in vitro or in vivo (via the generation of transgenic animals). For the purposes of the present invention, the term "essentially every gene" shall refer to the statistical situation where there is generally at least about a 70 percent probability that the genomes of cells used to construct the library collectively contain at least one inserted vector sequence in each gene, preferably a 85 percent probability, and more specifically at least about a 95 percent probability as determined by a standard Poisson distribution.

Also for the purposes of the present invention the term "gene" shall refer to any and all discrete coding regions of the cell's genome, as well as associated noncoding and regulatory regions. Additionally, the term operatively positioned shall refer to the control elements or genes that are provided with the proper orientation and spacing to provide the desired or indicated functions of the control elements or genes.

For the purposes of the present invention, a gene is "expressed" when a control element in the cell mediates the production of functional or detectable levels of mRNA encoded by the gene, or a selectable marker inserted therein. A gene is not expressed where the control element in the cell is absent, has been inactivated, or does not mediate the production of functional or detectable levels of mRNA encoded by the gene, or a selectable marker inserted therein.

5.1. Vectors Used to Build the Library

A number of investigators have developed gene trapping vectors and procedures for use in mouse and other cells (Allen et al., 1988; Bellen et al., 1989, Genes Dev. 3(9): 1288–1300; Bier et al., 1989, Genes Dev. 3(9):1273–1287; Bonnerot et al., 1992, J. Virol. 66(8):4982–4991; Brenner et al., 1989; Chang et al., 1993; Friedrich and Soriano, 1993; Friedrich and Soriano, 1991; Goff, 1987, Methods Enzymol. 152:469–481; Gossler et al.; Hope, 1991; Kerr et al., 1989; Reddy et al., 1991; Reddy et al., 1992; Skarnes et al., 1992; von Melchner and Ruley; Yoshida et al., 1995). The gene trapping system described in the present invention is based on significant improvements to the published SA (splice acceptor) DNA vectors and the ROSA (reverse orientation, splice acceptor) retroviral vectors (Chen et al., 1994; Friedrich and Soriano, 1991 and 1993). The presently described vectors also use a selectable marker called βgeo. This gene encodes a protein which is a fusion between the (β-galactosidase and neomycin phosphotransferase proteins. The presently described vectors place a splice acceptor sequence upstream from the βgeo gene and a polyadenylation signal sequence downstream from the marker. The marker is integrated after transfection by, for example, electroporation (DNA vectors), or retroviral infection, and gene trap events are selected based on resistance to G418 resulting from activation of βgeo expression by splicing from the endogenous gene into the ROSA splice acceptor. This type of integration disrupts the transcription unit and preferably results in a null mutation at the locus.

Although gene trapping has proven a useful analytical tool, the present invention contemplates gene trapping on a large scale. The vectors utilized in the present invention have been engineered to overcome the shortcomings of the early gene trap vector designs, and to facilitate procedures allowing high throughput. In addition, procedures are described that allow the rapid and facile acquisition of sequence information from each trapped cDNA which may be adapted to allow complete automation. These latter procedures are also designed for flexibility so that additional molecular information can easily be obtained subsequently. The present invention therefore incorporates gene trapping into a larger and unique tool. A specially organized set of gene trap clones that provide a novel and powerful new tool of genetic analysis.

The presently described vectors are superficially similar to the ROSA family of vectors, but constitute significant improvements and provide for additional features that are useful in the construction and indexing of the Library. Typically, gene trapping vectors are designed to detect insertions into transcribed gene regions within the genome. They generally consist of a selectable marker whose normal expression is handicapped by exclusion of some element required for proper transcription. When the vector integrates into the genome, and acquires the necessary element by juxtaposition, expression of the selectable marker is activated. When such activation occurs, the cell can survive when grown in the appropriate selective medium which allows for the subsequent isolation and characterization of the trapped gene. Integration of the gene trap generally causes the gene at the site of integration to be mutated.

Some gene trapping vectors have a splice acceptor preceding a selectable marker and a poly-adenylation signal following the selectable marker, and the selectable marker gene has its own initiator ATG codon. Using this arrangement, the fusion transcripts produced after integration generally only comprise exons 5' to the insertion site to the known marker sequences. Where the vector has inserted into the 5' region of the gene, it is often the case that the only exon 5' to the vector is a non-coding exon. Accordingly, the sequences obtained from such fusions do not provide the desired sequence information about the relevant gene products. This is because untranslated sequences are generally less well conserved than coding sequences.

To compensate for the short-comings of earlier vectors, the vectors of the present invention have been designed so that 3' exons are appended to the fusion transcript by replacing the poly-adenylation and transcription termination signals of earlier ROSA vectors with a splice donor (SD) sequence. Consequently transcription and splicing generally results in a fusion with all or most of the endogenous transcript and the selectable marker exon, for example βgeo, neomycin (neo) or puromycin (puro). The exon sequences immediately 3' to the selectable marker exon may then be sequenced and used to establish a database of expressed sequence tags. The presently described procedures will typically provide approximately 200 nucleotides of sequence, or more. These sequences will generally be coding and therefore informative. The prediction that the sequence obtained will be from coding region is based on two factors. First, gene trap vectors are generally found near the 5' end of the gene immediately after untranslated exons because the method selects for integration events that place the initiator ATG of the selectable marker as the first encountered, and thus used, for translation. Second, mammalian transcripts have short 5' untranslated regions (UTRs) which are typically between 50 and 150 nucleotides in length.

The obtained sequence information also provides a ready source of probes that may be used to isolate the full-length gene or cDNA from the host cell, or as heterologous probes for the isolation of homologous genes in other species.

Internal exons in mammalian transcripts are generally quite small, on the average 137 bases with few over 300 bases. Consequently, a large internal exon may be spliced less efficiently. Thus, the presently described vectors have been designed to sandwich relatively small selectable markers (for example: neo ,~800 bases, or a smaller drug resistance gene such as puro , ~600 bases) between the requisite splicing elements to produce relatively small exons. Exons of this size are more typical of mammalian exons and do not present undue problems for the splicing machinery of the cell. Such a design consideration is novel to the presently disclosed gene trapping vectors. Accordingly, an additional embodiment of the claimed vectors is that the respective splice acceptor and splice donor sites are engineered such that they are operatively positioned close to the ends of the selectable marker coding region (the region spanning from the initiation codon to the termination codon). Generally, the splice acceptor or splice donor sequences shall appear within about. 80 bases from the nearest end of the selectable marker coding region, preferably within about 50 bases from the nearest end of the coding region, more preferably within about 30 bases from the nearest end of the coding regions and specifically within about 20 bases of the nearest end of the selectable marker coding region.

The new vectors are represented in retroviral form in FIG. 1. They are used by infecting target cells with retroviral particles such that the proviruses shown in the schematic can be found in the genome of the target. These vectors are called VICTR which is an acronym for "viral constructs for trapping".

The presently described retroviral vectors may be used in conjunction with retroviral packaging cell lines such as those described in U.S. Pat. No. 5,449,614 ("'614 patent") issued Sep. 12, 1995, herein incorporated by reference. Where non-mouse animal cells are to be used as targets for generating the described libraries, packaging cells producing retrovirus with amphotropic envelopes will generally be employed to allow infection of the host cells.

The mutagenic gene trap DNA may also be introduced into the target cell genome by various transfection techniques which are familiar to those skilled in the art such as electroporation, lipofection, calcium phosphate precipitation, infection, retrotransposition, and the like. Examples of such techniques may be found in Sambrook et al. (1989) *Molecular Cloning Vols*. I–III, Cold Spring Harbor Laboratory Press, Cold Spring Harbor, N.Y., and *Current Protocols in Molecular Biology* (1989) John Wiley & Sons, all Vols. and periodic updates thereof, herein incorporated by reference. The transfected versions of the retroviral vectors are typically plasmid DNA molecules containing DNA cassettes comprising the described features between the retroviral LTRs.

The vectors VICTR 1 and 2 (FIG. 1) are designed to trap genes that are transcribed in the target cell. To trap genes that are not expressed in the target cell, gene trap vectors such as VICTR 3, 4 and 5 (described below) are provided. These vectors have been engineered to contain a promoter element capable of initiating transcription in virtually any cell type which is used to transcribe the coding sequence of the selectable marker. However, in order to get proper translation of the marker product, and thus render the cell resistant to the selective antibiotic, a polyadenylation signal and a transcription termination sequence must be provided. Vectors VICTR 3 through 5 are constructed such that an effective polyadenylation signal can only be provided by splicing with an externally provided downstream exon that contains a poly-adenylation site. Therefore, since the selectable marker coding region ends only in a splice donor sequence, these vectors must be integrated into a gene in order to be properly expressed. In essence, these vectors append the foreign exon encoding the marker to the 5' end of an endogenous transcript. These events will tag genes and create mutations that are used to make clones that will become part of the Library.

With the above design considerations, the VICTR series of vectors, or similarly designed and constructed vectors, have the following features. VICTR 1 is a terminal exon gene trap. VICTR 1 does not contain a control region that effectively mediates the expression of the selectable marker gene. Instead, the coding region of the selectable marker contained in VICTR 1, in this case encoding puromycin resistance (but which can be any selectable marker functional in the target cell type), is preceded by a splice acceptor sequence and followed by a polyadenylation addition signal sequence. The coding region of the puro gene has an initiator ATG which is downstream and adjacent to a region of sequence that is most favorable for translation initiation in eukaryotic cells—the so called Kozak consensus sequence (Kozak, 1989, J. Cell, Biol. 108(2):229–241). With a Kozak sequence and an initiator ATG, the puro gene in VICTR 1 is activated by integrating into the intron of an active gene, and the resulting fusion transcript is translated beginning at the puromycin initiation (ATG/AUG) codon. However, terminal gene trap vectors need not incorporate an initiator ATG codon. In such cases, the gene trap event requires splicing and the translation of a fusion protein that is functional for the selectable marker activity. The inserted puromycin coding sequence muse therefore be translated in the same frame as the "trapped" gene.

The splice acceptor sequence used in VICTR 1 and other members of the VICTR series is derived from the adenovirus major late transcript splice site located at the intron 1/exon 2 boundary. This sequence contains a polypyrimidine stretch preceding the AG dinucleotide which denotes the actual splice site. The presently described vectors contemplate the use of any similarly derived splice acceptor sequence. Preferably, the splice acceptor site will only rarely, if ever, be involved in alternative splicing events.

The polyadenylation signal at the end of the puro gene is derived from the bovine growth hormone gene. Any similarly derived polyadenylation signal sequence could be used if it contains the canonical AATAAA and can be demonstrated to terminate transcription and cause a polyadenylate tail to be added to the engineered coding exons.

VICTR 2 is a modification of VICTR 1 in which the polyadenylation signal sequence is removed and replaced by a splice donor sequence. Like VICTR 1, VICTR 2 does not contain a control region that effectively mediates the expression of the selectable marker gene. Typically, the splice donor sequence to be employed in a VICTR series vector shall be determined by reference to established literature or by experimentation to identify which sequences properly initiate splicing at the 5' end of introns in the desired target cell. The specifically exemplified sequence, AGGTAAGT, results in splicing occurring in between the two G bases. Genes trapped by VICTR 2 splice upstream exons onto the puro exon and downstream exons onto the end of the puro exon. Accordingly, VICTR 2 effectively mutates gene expression by inserting a foreign exon in-between two naturally occurring exons in a given transcript. Again, the puro gene may or may not contain a consensus Kozak translation initiation sequence and properly positioned ATG initiation codon. As discussed above, gene trapping by VICTR 1 and VICTR 2 requires that the mutated gene is expressed in the target cell line. By incorporating a splice donor into the VICTR traps, transcript sequences downstream from the gene trap insertion can be determined. As described above, these sequences are generally more informative about the gene mutated since they are more likely to be coding sequences. This sequence information is gathered according to the procedures described below.

VICTR 3, VICTR 4 and VICTR 5 are gene trap vectors that do not require the cellular expression of the endogenous trapped gene. The VICTR vectors 3 through 5 all comprise a promoter element that ensures that transcription of the selectable marker would be found in all cells that have taken up the gene trap DNA. This transcription initiates from a promoter, in this case the promoter element from the mouse phosphoglycerate kinase (PGK) gene. However, since the constructs lack a polyadenylation signal there can be no proper processing of the transcript and therefore no translation. The only means to translate the selectable marker and get a resistant cell clone is by acquiring a polyadenylation signal. Since polyadenylation is known to be concomitant with splicing, a splice donor is provided at the end of the selectable marker. Therefore, the only positive gene trap events using VICTR 3 through 5 will be those that integrate into a gene's intron such that the marker exon is spliced to downstream exons that are properly polyadenylated. Thus genes mutated with the VICTR vectors 3 through 5 need not be expressed in the target cell, and these gene trap vectors can mutate all genes having at least one intron. The design of VICTR vectors 3 through 5 requires a promoter element that will be active in the target cell type, a selectable marker and a splice donor sequence. Although a specific promoter was used in the specific embodiments, it should be understood that appropriate promoters may be selected that are known to be active in a given cell type. Typically, the considerations for selecting the splice donor sequence are identical to those discussed for VICTR 2, supra.

VICTR 4 differs from VICTR 3 only by the addition of a small exon upstream from the promoter element of VICTR 4. This exon is intended to stop normal splicing of the mutated gene. It is possible that insertion of VICTR 3 into an intron might not be mutagenic if the gene can still splice between exons, bypassing the gene trap insertion. The exon in VICTR 4 is constructed from the adenovirus splice acceptor described above and the synthetic splice donor also described above. Stop codons are placed in all three reading frames in the exon, which is about 100 bases long. The stops would truncate the endogenous protein and presumably cause a mutation.

A conceptually similar alternative design uses a terminal exon like that engineered into VICTR 5. Instead of a splice donor, a polyadenylation site is used to terminate transcription and produce a truncated message. Stops in all three frames are also provided to truncate the endogenous protein as well as the resulting transcript.

VICTR 20 is a modified version of VICTR 3 that incorporates a polyadenylation site 5' to the PGK promoter, the IRESβgeo sequence (i.e., foreign mutagenic polynucleotide sequence) 5' to the polyadenylation site, and a splice acceptor site 5' to the IRESβgeo coding region. VICTR 20 additionally incorporates, in operable combination, a pair of recombinase recognition sites that flank the PGKpuroSD cassette.

All of the traps of the VICTR series are designed such that a fusion transcript is formed with the trapped gene. For all but VICTR 1, the fusion contains cellular exons that are located 3' to the gene trap insertion. All of the flanking exons may be sequenced according to the methods described in the following section. To facilitate sequencing, specific sequences are engineered onto the ends of the selectable marker (e.g., puromycin coding region). Examples of such sequences include, but are not limited to unique sequences for priming PCR, and sequences complementary to the standard M13 forward sequencing primer. Additionally, stop codons are added in all three reading frames to ensure that no anomalous fusion proteins are produced. All of the unique 3' primer sequences are followed immediately by the synthetic 9 base pair splice donor sequence. This keeps the size of the exon comprising the selectable marker (puro gene) at a minimum to best ensure proper splicing, and positions the amplification and sequencing primers immediately adjacent to the flanking "trapped" exons to be sequenced as part of the construction of a Library database.

When any members of the VICTR series are constructed as retroviruses, the direction of transcription of the selectable marker is opposite to that of the direction of the normal transcription of the retrovirus. The reason for this organization is that the transcription elements such as the polyadenylation signal, the splice sites and the promoter elements found in the various members of the VICTR series interfere with the proper transcription of the retroviral genome in the packaging cell line. This would eliminate or significantly reduce retroviral titers. The LTRs used in the construction of the packaging cell line are self-inactivating. That is, the enhancer element is removed from the 3' U3 sequences such that the proviruses resulting from infection would not have an enhancer in either LTR. An enhancer in the provirus may otherwise affect transcription of the mutated gene or nearby genes.

Since a 'cryptic' splice donor sequence is found in the inverted LTRs, this splice donor sequence has been removed from the VICTR vectors by site specific mutagenesis. It was deemed necessary to remove this splice donor so that it would not affect the trapping splicing events.

The present disclosure also describes vectors that incorporate a new way to conduct positive selection. VICTR 3 and VICTR 20 are two examples of such vectors. Both VICTR 3 and VICTR 20, contain PGKpuroSD which must splice into exons of gene that provide a polyadenylation addition sequence in order to allow expression of the puromycin selectable marker gene. When placed in a targeting vector, PGKpuroSD allows for positive selection when targeting takes place. In addition to providing positive selection, targeted events among resistant colonies are easy to identify by the 3' RACE protocols (see section 5.2.2., infra) used for Omnibank production. This automated process allows for the rapid identification of targeted events. It is important that unlike SAβgeo, PGKpuroSD does not require expression of the targeted gene in order to provide positive selection. In addition, VICTR 20 provides 2 potential positive selectable markers (puro and neo). The use of two selectable markers, when a gene is expressed, provides a means to increase the targeting efficiency by requiring both selectable markers to function which is much more remote a possibility than having one selectable marker function unless there is a targeted event. The addition of a negative selection cassette to these vectors would only increase their targeting efficiency.

An additional feature that may be incorporated into the presently described vectors includes the use of recombinase recognition sequences. Bacteriophage P1 Cre recombinase and flp recombinase from yeast plasmids are two examples of site-specific DNA recombinase enzymes which cleave DNA at specific target sites (loxP sites for cre recombinase and frt sites for flp recombinase) and catalyze a ligation of this DNA to a second cleaved site. When a piece of DNA is flanked by 2 loxP or frt sites (e.g., recombinase control elements) in the same orientation, the corresponding recombinase will cause the removal of the intervening DNA sequence. When a piece of DNA is flanked by loxP or frt sites in an indirect orientation, the corresponding recombinase will essentially activate the control elements to cause the intervening DNA to be flipped into the opposite orientation. These recombinases provide powerful approaches for manipulating DNA in situ.

Recombinases have important applications for gene trapping and the production of a library of trapped genes. When constructs containing PGKpuroSD are used to trap genes, the fusion transcript between puromycin and sequences of the trapped gene could result in some level of protein expression from the trapped gene if translational reinitiation occurs. Another important issue is that several reports suggest that the PGK promoter can affect the expression of nearby genes. These effects may make it difficult to determine gene function after a gene trap event since one could not discern whether a given phenotype is associated with the inactivation of a gene, or the transcription of nearby genes.

Both potential problems are solved by exploiting recombinase activity. When PGKpuroSD is flanked by loxP, frt, or any other recombinase sites in the same orientation, the addition of the corresponding recombinase will result in the removal of PGKpuroSD. In this way, effects caused by PGKpuroSD fusion transcripts, or the PGK promoter, are avoided.

Accordingly, a vector that may be particularly useful for the practice of the present invention is VICTR 20. This vector replaces the terminal exon of VICTR 5 with a splice acceptor located upstream from the βgeo gene which can be used for both LacZ staining and antibiotic selection. The fusion gene possesses its own initiator methionine and an internal ribosomal entry site (IRES) for efficient translation initiation. In addition, the PGK promoter and puromycin-splice donor sequences have been flanked by lox P recombination sites. This allows for the ability to both remove and introduce sequences at the integration site and is of potential value with regard to the manipulation of regions proximal to trapped target genes (Barinaga, Science 265:26–8, 1994). While this particular vector includes lox P recombination sites, the present invention is in no way limited to the use of this specific recombination site (Akagi et al., Nucleic Acids Res 25:1766–73, 1997).

Another very important use of recombinases is to produce mutations that can be made tissue-specific and/or inducible. In the presently described vectors, the Saβgeo or SAIRESβgeo component provides the mutagenic function by "trapping" the normal splicing from preceding exons. If the SAβgeo is flanked by inverted loxP, frt, or any other recombinase sites, the addition of the corresponding recombinase results in the flipping of the SAβgeo sequence so that it no longer prevents the normal splicing of the cellular gene into which it is integrated. To make a gene trap tissue-specific or inducible one could produce the trap with SAβgeo in the reverse orientation and then provide recombinase activity only at the time and place where one wishes to remove the gene function. The use of tissue-specific or inducible recombinase constructs allows one to choose when and where one removes, or activates, the function of the targeted gene.

One method for practicing the inducible forms of recombinase mediated gene expression involves the use of vectors that use inducible or tissue specific promoter/operator elements to express the desired recombinase activity. The inducible expression elements are preferably operatively positioned to allow the inducible control or activation of expression of the desired recombinase activity. Examples of such inducible promoters or control elements include, but are not limited to, tetracycline, metallothionine, ecdysone, and other steroid-responsive promoters, rapamycin responsive promoters, and the like (No et al., Proc Natl Acad Sci USA 93:3345–51, 1996; Furth et al., Proc Natl Acad Sci USA 21:9302–6, 1994). Additional control elements that can be used include promoters requiring specific transcription factors such as viral, particularly HIV, promoters. Vectors incorporating such promoters would only express recombinase activity in cells that express the necessary transcription factors.

The incorporation of recombinase sites into the gene trapping vectors highlights the value of using the described gene trap vectors to deliver specific DNA sequence elements throughout the genome. Although a variety of vectors are available for placing sequences into the genome, the presently described vectors facilitate both the insertion of the specific elements, and the subsequent identification of where sequence has inserted into the cellular chromosome.

Additionally, the presently described vectors may be used to place recombinase recognition sites throughout the genome. The recombinase recognition sites could then be used to either remove or insert specific DNA sequences at predetermined locations.

Moreover, the described gene trap vectors can also be used to insert regulatory elements throughout the genome. Recent work has identified a number of inducible or repressible systems that function in the mouse. These include the rapamycin, tetracycline, ecdysone, glucocorticoid, and heavy metal inducible systems. These systems typically rely on placing DNA elements in or near a promoter. An inducible or repressible transcription factor that can identify and bind to the DNA element may also be engineered into the cells. The transcription factor will specifically bind to the DNA element in either the presence or absence of a ligand that binds to the transcription factor and, depending on the structure of the transcription factor, it will either induce or repress the expression of the cellular gene into which the DNA elements have been inserted. The ability to place these inducible or repressible elements throughout the genome would increase the value of the library by adding the potential to regulate the expression of the trapped gene.

The vectors described also have important applications for the overexpression of genes or portions of genes to select for phenotypic effects. Currently, overexpression of cDNA libraries to look for genes or parts of genes with specific functions is a common practice. One example would be to overexpress genes or portions of genes to look for expression that causes loss of contact inhibition for cell growth as determined by growth in soft agar. This would allow the identification of genes or portions of genes that can act as oncogenes. Simple modifications of VICTR 20 would allow it to be used for these applications. For example, the addition of an internal ribosome entry site (IRES) 3' to the puromycin selectable marker and before the SD sequence, would result in the overexpression of sequences from the trapped downstream exons. In addition, the IRES could be modified by, for example, the addition of one or two nucleotides such that there could be 3 basic vectors that would allow expression of trapped exons in all three reading frames. In this way, genes could be trapped throughout the genome resulting in overexpression of genes, or portions thereof, to examine the cellular function of the trapped genes. This identification of function could be done by selecting for the function of interest (i.e., growth in soft agar could result from the overexpression of potentially oncogenic genes). This technique would allow for the screening or selection of large numbers of genes, or portions thereof, by overexpressing the genes and identifying cells displaying the phenotypes of interest. Additional assays could, for example, identify candidate tumor suppressor genes based on their ability, when overexpressed, to prevent growth in soft agar.

Given the fact that expression pattern information can provide insight into the possible functions of genes mutated by the current methods, another LTR vector, VICTR 6, has been constructed in a manner similar to VICTR 5 except that the terminal exon has been replaced with either a gene coding for β-galactosidase (βgal) or a fusion between β-gal and neomycin phosphotransferase (βgeo), each proceeded by a splice acceptor and followed by a polyadenylation signal. Endogenous gene expression and splicing of these markers into cellular transcripts and translation into fusion proteins will allow for increased mutagenicity as well as the delineation of expression through Lac Z staining.

An additional vector, VICTR 12, incorporates two separate selectable markers for the analysis of both integration sites and trapped genes. One selectable marker (e.g. puro) is similar to that for VICTRs 3 through 5 in that it contains a promoter element at its 51' end and a splice donor sequence 3'. This gene cassette is located in the LTRs of the retroviral vector. The other marker (neo) also contains a promoter element but has a polyadenylation signal present at the 3' end of the coding sequence and is positioned between the viral LTRs. Both selectable markers contain an initiator ATG for proper translation. The design of VICTR 12 allows for the assessment of absolute titer as assayed by the number of colonies resistant to antibiotic selection for the constitutively expressed marker possessing a polyadenylation signal. This titer can then be compared to that observed for gene-trapping and stable expression of the resistance marker flanked at its 3' end by a splice donor. These numbers are important for the calculation of gene trapping frequency in the context of both nonspecific binding by retroviral integrase and directed binding by chimeric integrase fusions. In addition, it provides an option to focus on the actual integration sites through infection and selection for the marker containing the polyadenylation signal. This eliminates the need for the fusion protein binding to occur upstream and in the proximity of the target gene. Theoretically, any transcription factor binding sites present within the genome are targets for proximal integration and subsequent antibiotic resistance. Analysis of sequences flanking the LTRs of the retroviral vector should reveal canonical factor binding sites. In addition, by including the promoter/splice donor design of VICTR 3, gene-trapping abilities are retained in VICTR 12.

VICTR A is a vector which does not contain gene trapping constructs but rather a selectable marker possessing all of the required entities for constitutive expression including, but not limited to, a promoter element capable of driving expression in eukaryotic cells and a polyadenylation and transcriptional terminal signal. Similar to VICTR 12, downstream gene trapping is not necessary for successful selection using VICTR A. This vector is intended solely to select for successful integrations and serves as a control for the identification of transcription factor binding sites flanking the integrant as mentioned above.

Finally, VICTR B is similar to VICTR A in that it comprises a constitutively expressed selectable marker, but it also contains the bacterial β-lactamase ampicillin resistance selectable marker and a ColE1 origin of replication. These entities allow for the rapid cloning of sequences flanking the long terminal repeats through restriction digestion of genomic DNA from infected cells and ligation to form plasmid molecules which can be rescued by bacterial transformation, and subsequently sequenced. This vector allows for the rapid analysis of cellular sequences that contain putative binding sites for the transcription factor of interest.

Other vector designs contemplated by the present invention are engineered to include an inducible regulatory elements such as tetracycline, ecdysone, and other steroid-responsive promoters (No et al., Proc Natl Acad Sci USA 93:3345–51, 1996; Furth et al., Proc Natl Acad Sci USA 91:9302–6, 1994). These elements are operatively positioned to allow the inducible control of expression of either the selectable marker or endogenous genes proximal to site of integration. Such inducibility provides a unique tool for the regulation of target gene expression.

All of the gene trap vectors of the VICTR series, with the exception of VICTRs A and B, are designed to form a fusion transcript between vector encoded sequence and the trapped target gene. All of the flanking exons may be sequenced according to the methods described in the following section. To facilitate sequencing, specific sequences are engineered onto the ends of the selectable marker (e.g., puromycin coding region). Examples of such sequences include, but are not limited to unique sequences for priming PCR, and sequences complementary to standard M13 sequencing primers. Additionally, stop codons are added in all three reading frames to ensure that no anomalous fusion proteins are produced. All of the unique 3' primer sequences are immediately followed by a synthetic 9 base pair splice donor sequence. This keeps the size of the exon comprising the selectable marker at a minimum to ensure proper splicing, and positions the amplification and sequencing primers immediately adjacent to the flanking trapped exons to be sequenced as part of the generation of the collection of cells representing mutated transcription factor targets.

Since a cryptic splice donor sequence is found in the inverted LTRs, this cryptic splice donor sequence has been removed from the VICTR vectors by site specific mutagenesis. It was deemed necessary to remove this splice donor so that it would not affect trapping associated splicing events.

When any members of the VICTR series are packaged into infectious virus, the direction of transcription of the selectable marker is opposite to that of the direction of the normal transcription of the retrovirus. The reason for this organization is that the regulatory elements such as the polyadenylation signal, the splice sites and the promoter elements found in the various members of the VICTR series can interfere with the transcription of the retroviral genome in the packaging cell line. This potential interference may significantly reduce retroviral titers.

Although specific gene trapping vectors have been discussed at length above, the invention is by no means to be limited to such vectors. Several other types of vectors that may also be used to incorporate relatively small engineered exons into a target cell transcripts include, but are not limited to, adenoviral vectors, adenoassociated virus vectors, SV40 based vectors, and papilloma virus vectors. Additionally, DNA vectors may be directly transferred into the target cells using any of a variety of biochemical or physical means such as lipofection, chemical transfection, retrotransposition, electroporation, and the like.

Although, the use of specific selectable markers has been disclosed and discussed herein, the present invention is in no way limited to the specifically disclosed markers. Additional markers (and associated antibiotics) that are suitable for either positive or negative selection of eukaryotic cells are disclosed, inter alia, in Sambrook et al. (1989) *Molecular Cloning Vols.* I–III, Cold Spring Harbor Laboratory Press, Cold Spring Harbor, N.Y., and *Current Protocols in Molecular Biology* (1989) John Wiley & Sons, all Vols. and periodic updates thereof, as well as Table I of U.S. Pat. No. 5,464,764 issued Nov. 7, 1995, the entirety of which is herein incorporated by reference. Any of the disclosed markers, as well as others known in the art, may be used to practice the present invention.

5.2. The Analysis of Mutated Genes and Transcripts

The presently described invention allows for large-scale genetic analysis of the genomes of any organism for which there exists cultured cell lines. The Library may be constructed from any type of cell that can be transfected by standard techniques or infected with recombinant retroviral vectors.

Where mouse ES cells are used, then the Library becomes a genetic tool able to completely represent mutations in essentially every gene of the mouse genome. Since ES cells can be injected back into a blastocyst and become incorporated into normal development and ultimately the germ line, the cells of the Library effectively represent a complete panel of mutant transgenic mouse strains (see generally, U.S. Pat. No. 5,464,764 issued Nov. 7, 1995, herein incorporated by reference).

A similar methodology may be used to construct virtually any non-human transgenic animal (or animal capable of being rendered transgenic). Such nonhuman transgenic animals may include, for example, transgenic pigs, transgenic rats, transgenic rabbits, transgenic cattle, transgenic goats, and other transgenic animal species, particularly mammalian species, known in the art. Additionally, bovine, ovine, and porcine species, other members of the rodent family, e.g. rat, as well as rabbit and guinea pig and non-human primates, such as chimpanzee, may be used to practice the present invention.

Transgenic animals produced using the presently described library and/or vectors are useful for the study of basic biological processes and diseases including, but not limited to, aging, cancer, autoimmune disease, immune disorders, alopecia, glandular disorders, inflammatory disorders, diabetes, arthritis, high blood pressure, atherosclerosis, cardiovascular disease, pulmonary disease, degenerative diseases of the neural or skeletal systems, Alzheimer's disease, Parkinson's disease, asthma, developmental disorders or abnormalities, infertility, epithelial ulcerations, and microbial pathogenesis (a relatively comprehensive review of such pathogens is provided, inter alia, in Mandell et al., 1990, "principles and Practice of Infectious Disease" 3rd.,ed., Churchill Livingstone Inc., New York, N. Y. 10036, herein incorporated by reference)., As such, the described animals and cells are particularly useful for the practice of functional genomics.

5.2.1. Constructing a Library of Individually Mutated Cell Clones

The vectors described in the previous-section were used to infect (or transfect) cells in culture, for example, mouse embryonic stem (ES) cells. Gene trap insertions were initially identified by antibiotic resistance (e.g., puromycin). Individual clones (colonies) were moved from a culture dish to individual wells of a multi-welled tissue culture plate (e.g. one with 96 wells). From this platform, the clones were be duplicated for storage and subsequent analysis. Each multiwell plate of clones was then processed by molecular biological techniques described in the following section in order to derive sequence of the genre that has been mutated. This entire process is presented schematically in FIG. 4 (described below).

5.2.2. Identifying and Sequencing the Tagged Genes in the Library.

The relevant nucleic acid (and derived amino acid sequence information) will largely be obtained using PCR-'based' techniques that rely oh knowing part of the sequence of the fusion transcripts (see generally, Frohman et al., 1988, Proc. Natl. Acad. Sci. U.S.A. 85(23):8998–9000, and U.S. Pat. Nos. 4,683,195 to Saiki et al., and 4,683,202 to Mullis, which are herein incorporated by reference). Typically, such sequences are encoded by the foreign exon containing the selectable marker. The procedure is represented schematically in FIG. 2 (31 RACE). Although each step of the procedure may be done manually, the procedure is also designed to be carried out using robots that can deliver reagents to multi, well culture plates (e.g., but not limited to, 96-well plates).

The first step generates single stranded complementary DNA which is used in the PCR amplification reaction (FIG. 2). The RNA substrate for cDNA synthesis may either be total cellular RNA or an mRNA fraction; preferably the latter. mRNA was isolated from cells directly in the wells of the tissue culture dish. The cells were lysed and mRNA was bound by the complementary binding of the poly-adenylate tail to a poly-thymidine-associated solid matrix. The bound mRNA was washed several times and the reagents for the reverse transcription (RT) reaction were added. cDNA synthesis in the RT reaction was initiated at random positions along the message by the binding of a random sequence primer (RS). This RS primer has approximately 6–9 random nucleotides at the 3' end to bind sites in the mRNA to prime cDNA synthesis, and a 5' tail sequence of known composition to act as an anchor for PCR amplification in the next step. There is therefore no specificity for the trapped message in the RT step. Alternatively, a poly-dT primer appended with the specific sequences for the PCR may be used. Synthesis of the first strand of the cDNA initiates at the end of each trapped gene. At this point in the procedure, the bound mRNA may be stored (at between about −70° C. and about 40° C.) and reused multiple times. Such storage is a valuable feature where one subsequently desires to analyze individual clones in more detail. The bound mRNA may also be used to clone the entire transcript using PCR-based protocols.

Specificity for the trapped, fusion transcript is introduced in the next step, PCR amplification. The primers for this reaction are complementary to the anchor sequence of the RS primer and to the selectable marker. Double stranded fragments between a fixed point in the selectable marker gene and various points downstream in the appended transcript sequence are amplified. It is these fragments which will become the substrates for the sequencing reaction. The various end-points along the transcript sequence were determined by the binding of the random primer during the RT reaction. These PCR products were diluted into the sequencing reaction mix, denatured and sequenced using a primer specific for the splice donor sequences of the gene trap exon. Although, standard radioactively labeled nucleotides may be used in the sequencing reactions, sequences will typically be determined using standard dye terminator sequencing in conjunction with automated sequencers (e.g., ABI sequencers and the like).

Several fragments of various sizes may serve as substrates for the sequencing reactions. This is not a problem since the sequencing reaction proceeds from a fixed point as defined by a specific primer sequence. Typically, approximately 200 nucleotides of sequence were obtained for each trapped transcript. For the PCR fragments that are shorter than this, the sequencing reaction simply 'falls off' the end. Sequences further 3' were then covered by the longer fragments amplified during PCR. One problem is presented by the anchor sequences 'S' derived from the RS primer. When these are encountered during the sequencing of smaller fragments, they register as anomalous dye signals on the sequencing gels. To circumvent this potential problem, a restriction enzyme recognition site is included in the S sequence. Digestion of the double stranded PCR products with this enzyme prior to sequencing eliminates the heterologous S sequences.

5.2.3. Identifying the Tagged Genes by Chromosomal Location

Any individually tagged gene may also be identified by PCR using chromosomal DNA as the template. To find an individual clone of interest in the Library arrayed as described above, genomic DNA is isolated from the pooled clones of ES cells as presented in FIG. 3. One primer for the PCR is anchored in the gene trap vector, e.g., a puro exon-specific oligonucleotide. The other primer is located in the genomic DNA of interest. This genomic DNA primer may consist of either (1) DNA sequence that corresponds to the coding region of the gene of interest, or (2) DNA sequence from the focus or the gene of interest. In the first case, the only way that the two primers used may be juxtaposed to give a positive PCR results (e.g., the correct size double-stranded DNA product) is if the gene trap vector has inserted into the gene of interest. Additionally, degenerate primers may be used, to identify and isolate related genes of interest. In the second case, the only way that the two primers used may be juxtaposed to provide the desired PCR result is if the gene trap vector has inserted into the region of interest that contains the primer for the known marker.

For example, if one wishes to obtain ES cell clones from the library that contain mutated genes located in a certain chromosomal position, PCR primers are designed that correspond to the puro gene (the puro-anchored primer) and a primer that corresponds to a marker known to be located in the region of interest. Several different combinations of marker primers and primers that are located in the region of interest may also be used to obtain optimum results. In this manner, the mutated genes are identified by virtue of their location relative to sets of known markers. Genes in a particular chromosomal region of interest could therefore be identified. The marker primers could also be designed correspond to sequences of known genes in order to screen for mutations in particular genes by PCR on genomic DNA templates. While this method is likely to be less informative than the RT-PCR strategy described below, this technique would be useful as a alternative strategy to identify mutations in known genes. In addition, primers that correspond to sequence of known genes could be used in PCR reactions with marker-specific primers in order to identify ES cell clones that contain mutations in genes proximal to the known genes. The sensitivity of detection is adequate to find such events when positive clones are subsequently identified as described below in the RT-PCR strategy.

5.3. A Sequene Database identifies Genes Mutated in the Library.

Using the procedures described above, approximately 200 to about 600 bases of sequence from the cellular exons appended to the selectable marker exon (e.g., puro exon in VICTR vectors) may be identified. These sequences provide a means to identify and catalogue the genes mutated in each clone of the Library. Such a database provides both an index for the presently disclosed libraries, and a resource for discovering novel genes. Alternatively, various comparisons can be made between the Library database sequences and any other sequence database as would be familiar to those practiced in the art.

The novel utility of the Library lies in the ability for a person to search the Library database for a gene of interest based upon some knowledge of the nucleic acid or amino acid sequence. Once a sequence is identified, the specific clone in the Library can be accessed and used to study gene function. This is accomplished by studying the effects of the mutation both in vitro and in vivo. For example, cell culture systems and animal models (i.e., transgenic animals) may be directly generated from the cells found in the Library as will be familiar to those practiced in the art.

Additionally, the sequence information may be used to generate a highly specific probe for isolating both genomic clones from existing data bases, as well as a full length cDNA. Additionally, the probe may be used to isolate the homologous gene from sufficiently related species, including humans. Once isolated, the gene may be over expressed, or used to generate a targeted knock-out vector that may be used to generate cells and animals that are homozygous for the mutation of interest. Such animals and cells are deemed to be particularly useful as disease models (i.e., cancer, genetic abnormalities, AIDS, etc.), for developmental study, to assay for toxin susceptibility or the efficacy of therapeutic agents, and as hosts for gene delivery and therapy experiments (e.g., experiments designed to correct a specific genetic defect in vivo).

5.4. Accessing Clones in the Library by a Pooling and Screening Procedure.

An alternative method of accessing individual clones is by searching the Library database for sequences in order to isolate a clone of interest from pools of library clones. The Library may be arrayed either as single clones, each with different insertions, or as sets of pooled clones. That is, as many clones as will represent insertions into essentially every gene in the genome are grown in sets of a defined number. For example, 100,000 clones can be arrayed in 2,000 sets of 50 clones. This can be accomplished by titrating the number of VICTR retroviral particles added to each well of 96-well tissue culture plates. Two thousand clones will fit on approximately 20 such plates. The number of clones may be dictated by the estimated number of genes in the genome of the cells being used. For example, there are approximately 100,000 genes in the genome of mouse ES cells. Therefore, a Library of mutations in essentially every gene in the mouse genome may be arrayed onto 20 96-well plates.

To find an individual clone of interest in the Library arrayed in this manner, reverse transcription-polymerase chain reactions (RT-PCR) are performed on mRNA isolated from pooled clones as presented in FIG. 4. One primer for RT-PCR is anchored in the gene trap vector, i.e. a puro exon-specific oligonucleotide. The other primer is located in the cDNA sequence of a gene of interest. The only way that these two sequences can be juxtaposed to give a positive RT-PCR result (i.e. double stranded DNA fragment visible by agarose gel electrophoresis, as will be familiar to anyone practiced in the art) is by being present in a transcript from a gene trap event occurring in the gene of interest.

For example, if one wishes to obtain an ES cell clone with a mutation in the p53 gene, PCR primers are designed that correspond to the puro and p53 genes. If a VICTR trapping vector integrates into the p53 locus and results in the formation of a fusion mRNA, this mRNA may be detected by RT-PCR using these specifically designed primer pairs. The sensitivity of detection is adequate to find such an event when positive cells are mixed with a large background of negative cells. The individual positive clones are subsequently identified by first locating the pool of 50 clones in which it resides. This process is described in FIG. 5. The positive pool, once identified, is subsequently plated at limiting dilution (approximately 0.3 cells/well) such that individual clones may be isolated. To find the one positive event in 50 clones represented by this pool, individual clones are isolated and arrayed on a 96-well plate. By pooling in columns and rows, the positive well containing the positive clone can be identified with relatively few RT-PCR reactions.

In addition to RT-PCR, the pools may be screened by hybridization techniques (see generally Sambrook et al., 1989, *Molecular Cloning: H Laboratory Manual* 2nd edition, Cold Spring Harbor Press, Cold Spring Harbor, and *Current Protocols in Molecular Biology*, 1995, Ausubel et al. eds., John Wiley and Sons). Specific PCR fragments are generated from the mutated genes essentially as described above for the sequencing protocols of the individual clones (first-strand synthesis using RT primed by a random or oligo dT primer that is appended to a specific primer binding site). The gene trap DNA is amplified from the primer sets in the puro gene and the specific sequences appended to the RT primer. If this were done with pools, the resulting pooled set of amplified DNA fragments could be arrayed on membranes and probed by radioactive, or chemically or enzymatically labeled, hybridization probes specific for a gene of interest. A positive radioactive result indicates that the gene of interest has been mutated in one of the clones of the positively-labeled pool. The individual positive clone is subsequently identified by PCR or hybridization essentially as outlined above.

Alternatively, a similar strategy may be used to identify the clone of interest from multiple plates; or any scheme where a two or three dimensional array (e.g., columns and rows) of individual clones are pooled by row or by column. For example, 96 well plates of individual clones may be arranged adjacent to each other to provide a larger (or virtual/figurative) two dimensional grid (e.g., four plates may be arranged to provide a net 16×24 grid), and the various rows and columns of the larger grid may be pooled to achieve substantially the same result.

Similarly, plates may simply be stacked, literally or figuratively, or arranged into a larger grid and stacked to provide three dimensional arrays of individual clones. Representative pools from all three planes of the three dimensional grid may then be analyzed, and the three positive pools/planes may be aligned to identify the desired clone. For example, ten 96 well plates may be screened by pooling the respective rows and columns from each plate (a total of 20 pools) as well as pooling all of the clones on each specific plate (10 additional pools). Using this method, one may effectively screen 960 clones by performing PCR on only 30 pooled samples.

The example provided below is merely illustrative of the subject invention. Given the level of skill in the art, one may be expected to modify any of the above or following disclosure to produce insubstantial differences from the specifically described features of the present invention. As such, the following example is provided solely by way of illustration and is not included for the purpose of limiting the invention in any way whatsoever.

6.0. EXAMPLES 6.1. Use of VICTR Series Vectors to Construct a Mouse ES Cell Gene Trap Library VICTR 3 was used to gather a set of gene trap clones. A plasmid containing the VICTR 3 cassette was constructed by conventional cloning techniques and designed to employ the features described above. Namely, the cassette contained a PGK promoter directing transcription of an exon that encodes the puro marker and ends in a canonical splice donor sequence. At the end of the puromycin exon, sequences were added as described that allow for the annealing of two nested PCR and sequencing primers. The vector backbone was based on pBluescript KS+ from, Stratagene Corporation.

The plasmid construct linearized by digestion with Sca I which cuts at a unique site in the plasmid backbone. The plasmid was then transfected into the mouse ES cell line AB2.2 by electroporation using a BiORad Genepulser apparatus. After the cells were allowed to recover, gene trap clones were selected by adding puromycin to the medium at a final concentration of 3 $\mu$g/mL. Positive clones were allowed to grow under selection for approximately 10 days before being removed and cultured separately for storage and to determine the sequence of the disrupted gene.

Total RNA was isolated from an aliquot of cells from each of 18 gene trap clones chosen for study. Five micrograms of this RNA was used in a first strand cDNA synthesis reaction using the "RS" primer. This primer has unique sequences (for subsequent PCR) on its 5' end and nine random nucleotides or nine T (thymidine) residues on it's 3' end. Reaction products from the first strand synthesis were added directly to a PCR with outer primers specific for the engineered sequences of puromycin and the "RS" primer. After amplification, an aliquot of reaction products were subject to a second round of amplification using primers internal, or nested, relative to the first set of PCR primers. This second amplification provided more reaction product for sequencing and also provided increased specificity for the specifically gene trapped DNA.

The products of the nested PCR were visualized by agarose gel electrophoresis, and seventeen of the eighteen clones provided at least one band that was visible on the gel with ethidium bromide staining. Most gave only a single band which is an advantage in that a single band is generally easier to sequence. The PCR products were sequenced directly after excess PCR primers and nucleotides were removed by filtration in a spin column (Centricon-100, Amicon). DNA was added directly to dye terminator sequencing reactions (purchased from ABI) using the standard M13 forward primer a region for which was built into the end of the puro exon in all of the PCR fragments. Thirteen of the seventeen clones that gave a band after the PCR provided readable sequence. The minimum number of readable nucleotides was 207 and some of the clones provided over 500 nucleotides of useful sequence.

Sample data from this set of clones is presented in FIG. 6. Only a portion of sequence (nucleotide or putative amino acid) for 9 Library clones obtained by the methods described in this invention are presented. Under each sequence fragment in the figure is aligned a homologous sequence that was identified using the BLAST (basic local alignment search tool) search algorithm (Altschul et al., 1990, J. Mol. Biol. 215:403–410).

In addition to known sequences, many new genes were also identified. Each of these sequences is labeled "OST" for "Omnibank Sequence Tags." OMNIBANK™ shall be the trademark name for the Libraries generated using the disclosed technology.

These data demonstrate that the VICTR series vectors may efficiently trap genes, and that the procedures used to obtain sequence are reliable. With simple optimization of each step, it is presently possible to mutate every gene in a given population of cells, and obtain sequence from each of these mutated genes. The sample data provided in this example represents a small fraction of an entire Library. By simply performing the same procedures on a larger scale (with automation) a Library may be constructed that collectively comprises and indexes mutations in essentially every gene in the genome of the target cell.

Additional studies have used both VICTR 3 and VICTR 20. Like VICTR 3, VICTR 20 is exemplary of a family of vectors that incorporate two main functional units: a 1) sequence acquisition component having a strong promoter element (phosphoglycerate kinase 1) active in ES cells that is fused to the puromycin resistance gene coding sequence which lacks a polyadenylation sequence but is followed by a synthetic consensus splice donor sequence (PGKpuroSD); and 2) a mutagenic component that incorporates a splice acceptor sequence fused to a selectable, calorimetric marker gene and followed by a polyadenylation sequence (for example, SAβgeopA or SAIRESβgeopA). Also like VICTR 3, stop codons have been engineered into all three reading frames in the region between the 3' end of the selectable marker and the splice donor site. A diagrammatic description of structure and functions of VICTRs 3 and 20 is provided in FIG. 7.

When VICTRs 3 and 20 were used in the commercial scale application of the presently disclosed invention, over 3,000 mutagenized ES cell clones were rapidly engineered and obtained. Sequence analysis obtained from these clones has identified a wide variety of both previously identified and novel sequences. A representative sampling of previously known genes that were identified using the presently described methods is provided in FIG. 8. The power of the presently described invention as a genomics resource becomes apparent when one considers that the genes listed in FIG. 8 were obtained and identified in less than a year whereas the references associated with the identification of the known genes span a period of roughly two decades. More importantly, the majority of the sequences thus far identified are novel, and, because of the functional aspects of the presently described ES cell system, the cellular and developmental functions of these novel sequences can be rapidly established.

The following plasmids have been deposited at the American Type Culture Collection (ATCC), Manassas, Va., USA, under the terms of the Budapest Treaty on the International Recognition of the Deposit of Microorganisms for the Purpose of Patent Procedure and Regulations there under (Budapest Treaty) and are thus maintained and made available according to the terms of the Budapest Treaty. Availability of such plasmids is not to be construed as a license to practice the invention in contravention of the rights granted under the authority of any government in accordance with its patent laws.

The deposited cultures have been assigned the indicated ATCC deposit numbers:

| Plasmid | ATCC No. |
| --- | --- |
| plex | 97748 |
| pExonII | 97749 |
| ppuro7 | 97750 |
| ppuro5 | 97751 |
| ppuro11 | 97752 |
| ppuro10 | 97753 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

What is claimed is:

1. A library of cultured eucaryotic cells comprising at least two subpopulations of cells, wherein the at least two subpopulations of cells comprises
   (a) a first subpopulation of cells, wherein cells of the first subpopulation have a first vector integrated nonspecifically into their genomes, wherein the first vector mediates the splicing of a foreign exon internal to a cellular transcript, and wherein the first vector comprises:
      (i) a foreign exon,
      (ii) a splice acceptor site operatively positioned 5' to said foreign exon, and
      (iii) a splice donor site operatively positioned 3' to said foreign exon, wherein the first vector does not comprise a promoter operatively positioned 5' to said foreign exon; and
   (b) a second subpopulation of cells, wherein cells of the second subpopulation have a second vector integrated nonspecifically into their genomes, wherein the second vector mediates the splicing of a foreign exon 5' to an exon of a cellular transcript, and wherein the second vector comprises:
      (i) a foreign exon,
      (ii) a promoter operatively positioned 5' to said foreign exon,
      (iii) a splice donor site operatively positioned 3' to said foreign exon; and
      (iv) a mutagenic foreign polynucleotide sequence located upstream from said promoter.

2. The library of claim 1 wherein said cultured eucaryotic cells are animal cells.

3. The library of claim 2 wherein said cultured eucaryotic cells are mammalian cells.

4. The library of claim 3 wherein said cultured eucaryotic cells are rodent cells.

5. The library of claim 4 wherein said cultured eucaryotic cells are mouse cells.

6. The library of claim 1, wherein said cultured eucaryotic cells are organized into individual clones.

* * * * *

SEQUENCE LISTING

<160> NUMBER OF SEQ ID NOS: 18

<210> SEQ ID NO 1
<211> LENGTH: 55
<212> TYPE: DNA
<213> ORGANISM: Mus musculus

<400> SEQUENCE: 1
tttatataat atttaatttg ttttactggg gtatatatgt gtgaagagga cttct    55

<210> SEQ ID NO 2
<211> LENGTH: 55
<212> TYPE: DNA
<213> ORGANISM: Rattus norvegicus

<400> SEQUENCE: 2
tttacataat atttaatttg ttttactggg gtatatatgt gtgaagagga ctttt    55

<210> SEQ ID NO 3
<211> LENGTH: 60
<212> TYPE: DNA
<213> ORGANISM: Mus musculus
<220> FEATURE:
<221> NAME/KEY: misc_feature
<222> LOCATION: (49)..(49)
<223> OTHER INFORMATION: n is A, C, T, or G

<400> SEQUENCE: 3
accgttgcgg aggctcacgt ttctcagata gtacatcagg tgtcatcgnt gtcagaaggt    60

<210> SEQ ID NO 4
<211> LENGTH: 60
<212> TYPE: DNA
<213> ORGANISM: Mus musculus

<400> SEQUENCE: 4
accgttgcgg ggcctcacgt ttctcagata gtacatcagg tgtcatcgtt atcagaaagt    60

<210> SEQ ID NO 5
<211> LENGTH: 60
<212> TYPE: PRT
<213> ORGANISM: Mus musculus
<220> FEATURE:
<221> NAME/KEY: misc_feature
<222> LOCATION: (22)..(22)
<223> OTHER INFORMATION: X is unknown amino acid

<400> SEQUENCE: 5

Gly Ile Gly Met His His Ala Gly Leu His Glu Arg Asp Arg Lys Thr
1               5                   10                  15

Val Glu Glu Leu Phe Xaa Asn Cys Lys Val Gln Val Leu Ile Ala Thr
            20                  25                  30

Ser Thr Leu Ala Trp Gly Val Asn Phe Pro Ala His Leu Val Ile Ile
        35                  40                  45

Lys Gly Thr Glu Tyr Tyr Asp Gly Lys Thr Arg Arg
    50                  55                  60

<210> SEQ ID NO 6
<211> LENGTH: 60
<212> TYPE: PRT
<213> ORGANISM: Saccharomyces cerevisiae

<400> SEQUENCE: 6

Gly Ile Gly Leu His His Ala Gly Leu Val Gln Lys Asp Arg Ser Ile
1               5                   10                  15

Ser His Gln Leu Phe Gln Lys Asn Lys Ile Gln Ile Leu Ile Ala Thr
                20                  25                  30

Ser Thr Leu Ala Trp Gly Val Asn Leu Pro Ala His Leu Val Ile Ile
            35                  40                  45

Lys Gly Thr Gln Phe Phe Asp Ala Lys Ile Glu Gly
50                  55                  60

<210> SEQ ID NO 7
<211> LENGTH: 60
<212> TYPE: DNA
<213> ORGANISM: Mus musculus
<220> FEATURE:
<221> NAME/KEY: misc_feature
<222> LOCATION: (14)..(14)
<223> OTHER INFORMATION: n is A, C, T, or G
<220> FEATURE:
<221> NAME/KEY: misc_feature
<222> LOCATION: (21)..(21)
<223> OTHER INFORMATION: n is A, C, T, or G
<220> FEATURE:
<221> NAME/KEY: misc_feature
<222> LOCATION: (25)..(25)
<223> OTHER INFORMATION: n is A, C, T, or G
<220> FEATURE:
<221> NAME/KEY: misc_feature
<222> LOCATION: (32)..(32)
<223> OTHER INFORMATION: n is A, C, T, or G
<220> FEATURE:
<221> NAME/KEY: misc_feature
<222> LOCATION: (57)..(57)
<223> OTHER INFORMATION: n is A, C, T, or G

<400> SEQUENCE: 7
gcgcagaagt ggtnctggaa ntttntccgc cnccatccag tctattaatt gttgacngga      60

<210> SEQ ID NO 8
<211> LENGTH: 60
<212> TYPE: DNA
<213> ORGANISM: Escherichia coli

<400> SEQUENCE: 8
gcgcagaagt ggtcctgcaa ctttatccgc ctccatccag tctattaatt gttgccggga      60

<210> SEQ ID NO 9
<211> LENGTH: 23
<212> TYPE: PRT
<213> ORGANISM: Mus musculus
<220> FEATURE:
<221> NAME/KEY: misc_feature
<222> LOCATION: (10)..(10)
<223> OTHER INFORMATION: X is unknown amino acid

<400> SEQUENCE: 9

Thr Cys Trp Ile Arg Leu Gly Thr Arg Xaa Val Gly Ala Ser Leu Glu
1               5                   10                  15

Tyr Glu Tyr Ile Arg Ala Ser
            20

<210> SEQ ID NO 10
<211> LENGTH: 24
<212> TYPE: PRT
<213> ORGANISM: Mus musculus

<400> SEQUENCE: 10

-continued

```
Thr Cys Trp Leu Gln Leu Ala Asp Phe Arg Lys Val Gly Asp Ala Leu
1               5                   10                  15
Lys Glu Lys Tyr Asp Ser Ala Ala
            20
```

```
<210> SEQ ID NO 11
<211> LENGTH: 60
<212> TYPE: DNA
<213> ORGANISM: Mus musculus

<400> SEQUENCE: 11
cttatatggc tacggcggct tcaacatctc cattacaccc aactacagcg tgtccaggct    60

<210> SEQ ID NO 12
<211> LENGTH: 60
<212> TYPE: DNA
<213> ORGANISM: Homo sapiens

<400> SEQUENCE: 12
cttatatggc tatggcggct tcaacatatc catcacaccc aactacagtg tttccaggct    60

<210> SEQ ID NO 13
<211> LENGTH: 60
<212> TYPE: DNA
<213> ORGANISM: Mus musculus

<400> SEQUENCE: 13
aaagcatgta gcagttgtag gacacactag acgagagcac cagatctcat tgtgggtggt    60

<210> SEQ ID NO 14
<211> LENGTH: 60
<212> TYPE: DNA
<213> ORGANISM: Mus musculus

<400> SEQUENCE: 14
aaagcatgta gcagttgtag gacacactag acgagagcac cagatctcat tgtgggtggt    60

<210> SEQ ID NO 15
<211> LENGTH: 60
<212> TYPE: DNA
<213> ORGANISM: Mus musculus
<220> FEATURE:
<221> NAME/KEY: misc_feature
<222> LOCATION: (10)..(10)
<223> OTHER INFORMATION: X is unknown amino acid

<400> SEQUENCE: 15
tggatgcagn ctaccactgt gtggctgccc tattttacct cagtgcctca gttctggaag    60

<210> SEQ ID NO 16
<211> LENGTH: 60
<212> TYPE: DNA
<213> ORGANISM: Rattus norvegicus

<400> SEQUENCE: 16
tggatgcagc ctaccactgt gtggctgccc tgttttacct cagtgcctca gtcctggaag    60

<210> SEQ ID NO 17
<211> LENGTH: 60
<212> TYPE: DNA
<213> ORGANISM: Mus musculus

<400> SEQUENCE: 17
acctgattgt tatccgtggc ctgcagaagt ccagaaaata cagaccaaag tcaaccagta    60
```

```
<210> SEQ ID NO 18
<211> LENGTH: 60
<212> TYPE: DNA
<213> ORGANISM: Mus musculus

<400> SEQUENCE: 18
acctgattgt tatccgtggc ctgcagaagt ccagaaaata cagaccaaag tcaaccagta        60
```